(12) United States Patent
Armour et al.

(10) Patent No.: US 7,597,889 B1
(45) Date of Patent: Oct. 6, 2009

(54) BINDING MOLECULES DERIVED FROM IMMUNOGLOBULINS WHICH DO NOT TRIGGER COMPLEMENT MEDIATED LYSIS

(75) Inventors: Kathryn Lesley Armour, Cambridge (GB); Michael Ronald Clark, Cambridge (GB); Lorna McLeod Williamson, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 0 days.

(21) Appl. No.: 09/674,857

(22) PCT Filed: May 7, 1999

(86) PCT No.: PCT/GB99/01441

§ 371 (c)(1), (2), (4) Date: Nov. 7, 2000

(87) PCT Pub. No.: WO99/58572

PCT Pub. Date: Nov. 18, 1999

(30) Foreign Application Priority Data

May 8, 1998 (GB) ................................. 9809951.8

(51) Int. Cl.
    A61K 39/395 (2006.01)
    A61K 39/00 (2006.01)
    C12P 21/08 (2006.01)
    C12N 15/11 (2006.01)
    C12N 15/13 (2006.01)
    C07K 16/28 (2006.01)
    C07K 16/34 (2006.01)
    C07H 15/00 (2006.01)

(52) U.S. Cl. ............... 424/133.1; 424/142.1; 424/143.1; 424/152.1; 424/171.1; 435/69.1; 435/320.1; 530/387.3; 530/388.1; 530/388.22; 530/388.25; 530/388.7; 530/388.75; 536/23.53; 536/24.33

(58) Field of Classification Search .............. 530/387.3, 530/387.5, 391.5, 391.9; 424/133.1; 435/69.1
    See application file for complete search history.

(56) References Cited

U.S. PATENT DOCUMENTS

| 5,624,821 | A |   | 4/1997  | Winter et al.     |           |
|-----------|---|---|---------|-------------------|-----------|
| 5,834,597 | A |   | 11/1998 | Tso et al.        |           |
| 5,846,534 | A | * | 12/1998 | Waldmann et al.   | 424/133.1 |
| 6,015,555 | A | * | 1/2000  | Friden            | 424/133.1 |
| 6,194,551 | B1|   | 2/2001  | Idusogie et al.   |           |

FOREIGN PATENT DOCUMENTS

| WO | WO 92/16562 |   | 10/1992 |
|----|-------------|---|---------|
| WO | WO 93/04173 |   | 3/1993  |
| WO | 94/28027    |   | 12/1994 |
| WO | WO94/29351  | * | 12/1994 |
| WO | 95/05468    |   | 2/1995  |
| WO | WO 95/05468 | * | 2/1995  |
| WO | 98/05787    |   | 2/1998  |

OTHER PUBLICATIONS

Ngo et al., 1994, The Protein Folding Problem and Tertiary Structure Prediction, pp. 492-495.*
Kuby et al, 1994, Immunology, Second edition, pp. 86-96.*
Riechmann et al, 1988, Nature 332: 323-327.*
Greenwood et al, Eur J Immunol 23: 1098-1104, 1993.*
Stryer et al, in Biochemistry, Third edition, W H Freeman Company, New York, pp. 31-33, 1998.*
Griffin et al, Blood 86: 4430, Dec. 1995.*
Warmerdam et al, "A Single Amino Acid in the Second Ig-Like Domain of the Human Fcγ Receptor II is Critical for Human IgG2 Binding", The Journal of Immunology 147(4):1338-1343 (1991).
Warmerdam et al, "Interaction of a human FcγRIIb1 (CD32) isoform with murine and human IgG subclasses", International Immunology 5(3):239-247 (1992).
Armour et al, "Recombinant IgG Lacking FcγRI Binding and Complement/Chemiluminescence Activation", 5th European Symposium on Platelet and Granulocyte Immunobiology, May 9-12, 1998.
Clark et al, "IgG Effector Mechanisms", Chem. Immunol. 65:88-110 (1997).
Morgan et al, "The N-terminal end of the $C_H2$ domain of chimeric human IgG1 and anti-HLA-DR is neccessary for C1q, FcγRI and FcγRIII binding", Immunology 86:319-324 (1995).
Chappel et al, "Identification of the Fcγ receptor class I binding site in human IgG through the use of recombinant IgG1/IgG2 hybrid and point-mutated antibodies", Proc. Natl. Acad. Sci. USA 88:9036-9040 (1991).

(Continued)

Primary Examiner—Phuong Huynh
(74) Attorney, Agent, or Firm—Nixon & Vanderhye P.C

(57) ABSTRACT

Disclosed are binding molecules which are recombinant polypeptides containing: (i) a binding domain capable of binding a target molecule, and (ii) an effector domain having an amino acid sequence substantially homologous to all or part of a constant domain of a human immunoglobulin heavy chain; characterized in that the binding molecule is capable of binding the target molecule without triggering significant complement dependent lysis, or cell mediated destruction of the target, and more preferably wherein the effector domain is capable of specifically binding FcRn and/or FcγRIIb. These are generally based on chimeric domains which are derived from two or more human immunoglobulin heavy chain CH2 domains domains. In preferred embodiments the regions 233-236, and 327-331, are modified, as are further residues to render the molecule null allotypic. Also disclosed are nucleic acids, host cells, production processes and materials, and uses. Pharmaceutical preparations are also disclosed.

52 Claims, 14 Drawing Sheets

OTHER PUBLICATIONS

Figure 1:
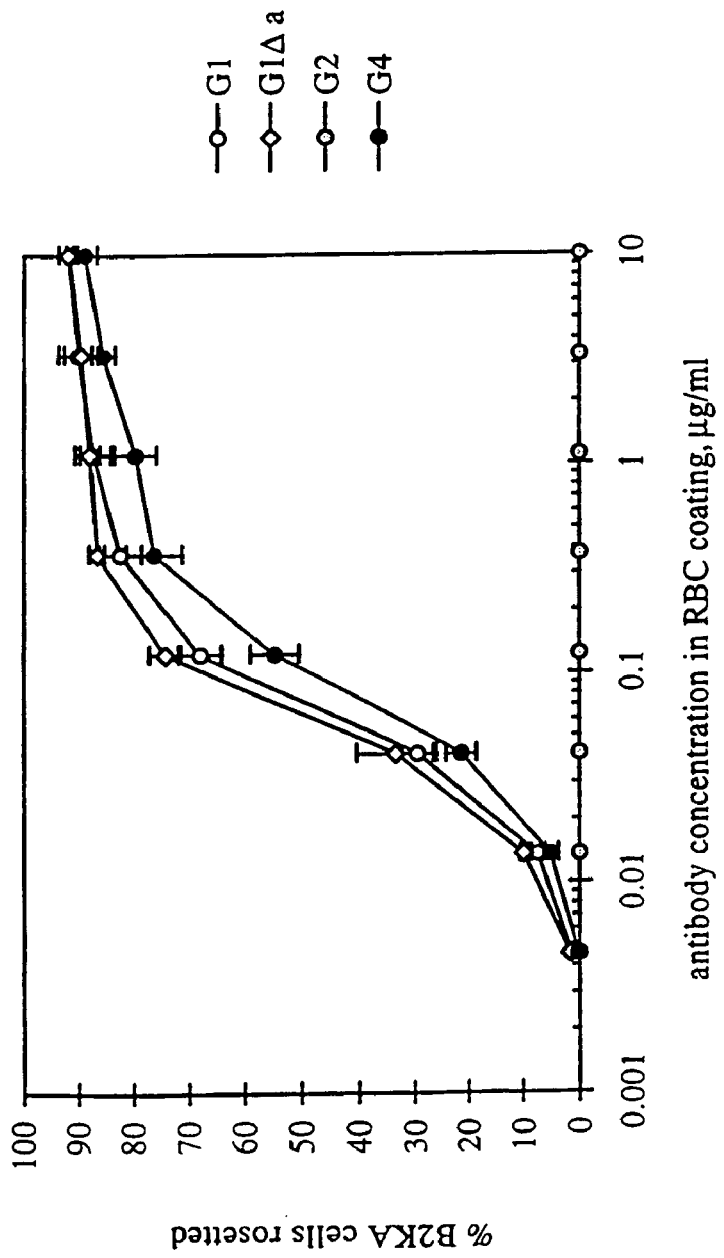

Armour K.L. et al.: "Recombinant human IgG molecules lacking Fc.gamma. receptor I binding and monocyte triggering activities." European Journal of Immunology, (Aug. 1999) 29/8 pp. 2613-2624.

Cole M.S. et al.: "Human IgG2 Variants of Chimeric Anti-CD3 Are Nonmitogenic to T Cells" The Amerian Association of Immunologists pp. 3613-3621, 1997.

Mueller J.P. et al. "Humanized porcine Vcam-specific monoclonal antibodies with chimeric IgG2/G4 Constant Regions Block Human Leukocyte Binding to Porcine Endothelial Cells" Alexion Pharmaceuticals Inc., Departments of Immunobiology and Molecular Development Molecular Immunology, vol. 34, No. 6, (1997) pp. 441-452.

Canfield and Morrison, "The Binding Affinity of Human IgG for its High Affinity Fc Receptor Is Determined by Multiple Amino Acids in the CH2 Domain and Is Modulated by the Hinge Region", J. Exp. Med. 173:1438-1491 (1991).

Tao et al, The Differential Ability of Human IgG1 and IgG4 to Activate Complement Is Determined by the COOH-terminal Sequence of the $C_H2$ Domain, Brief Definitive Report, J. Exp. Med., vol. 173, Apr. 1991, pp. 1025-1028.

Duncan and Winter (1988. Nature, 332: 738-740).

Valim and Lachmann (1991. Clin Exp Immunol, 84: 1-8).

Sarmay et al. (1992. Mol Immunol, 29: 633-639).

Michaelsen et al. (1992. Mol Immunol, 29: 319-326 ).

Dorai et al. (1992. Mol Immunol, 29: 1487-1491).

Wright and Morrison (1994. J Exp Med, 180: 1087-1096 ).

Brekke et al. (1995, Immunol Today, 16: 85-90 ).

Ward and Ghetie (1995. Therapeutic Immunology, 2: 77-94).

* cited by examiner

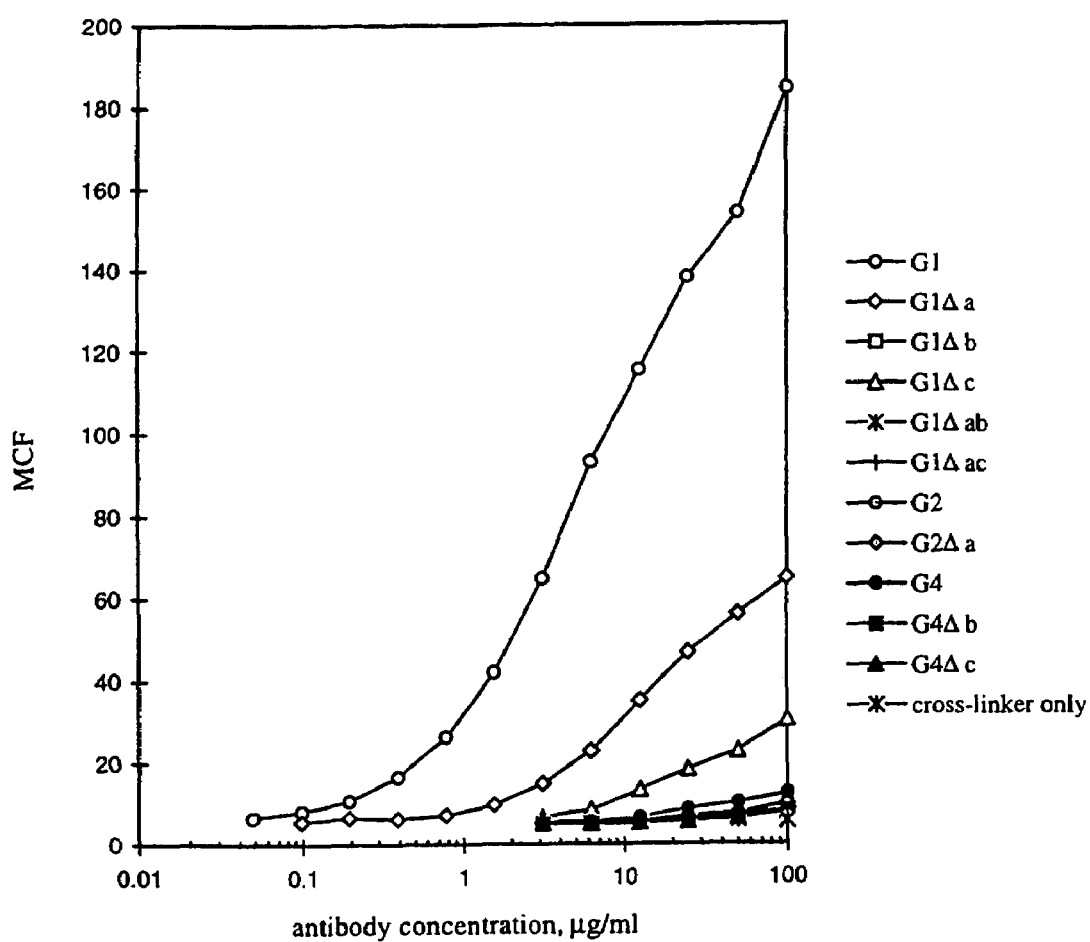

Table 1
A comparison of the mutations made to the wildtype G1, G2 and G4 antibodies

| Antibody | 233 | 234 | 235 | 236 | 327 | 330 | 331 |
|---|---|---|---|---|---|---|---|
| G1    | E | L | L | G | A | A | P |
| G1Δa  | E | L | L | G | G | S | S |
| G1Δb  | P | V | A | - | A | A | P |
| G1Δc  | P | V | A | G | A | A | P |
| G1Δab | P | V | A | - | G | S | S |
| G1Δac | P | V | A | G | G | S | S |
| G2    | P | V | A | - | G | A | P |
| G2Δa  | P | V | A | - | G | S | S |
| G4    | E | F | L | G | G | S | S |
| G4Δb  | P | V | A | - | G | S | S |
| G4Δc  | P | V | A | G | G | S | S |

Figure 16

| Assay system | Series | G1 | G1Δa | G1Δb | G1Δc | G1Δab | G1Δac | G2 | G2Δa | G4 | G4Δb | G4Δc |
|---|---|---|---|---|---|---|---|---|---|---|---|---|
| FcγRI: rosetting | F | +++ | +++ | - | -/+ | - | - | - | - | ++ | - | - |
| FcγRI: fluorescent staining | C/F | +++ | +++ | - | -/+ | - | -/+ | - | - | ++ | - | -/+ |
| FcγRIIa H/H: fluorescent staining | C/F | +++ | ++ | + | -/+ | + | -/+ | +++ | ++ | -/+ | -/+ | - |
| FcγRIIa R/R: fluorescent staining | F | +++ | +++ | +/- | +/- | + | +/- | ++ | ++ | +/- | +/- | -/+ |
| FcγRIIb1*: fluorescent staining | F | ++++ | ++++ | + | + | ++ | ++ | + | +++ | +++ | + | + |
| FcγRIIIb NA1: rosetting | F | ++ | + | +/- | +/- | -/+ | -/+ | +/- | - | +/- | - | - |
| FcγRIIIb NA1: fluor. staining | F | +++ | ++ | - | + | - | - | - | - | +/- | - | - |
| FcγRIIIb NA2: fluor. staining | F | +++ | ++ | - | + | - | - | - | - | +/- | - | - |
| FcγRI/II: chemiluminescence | F | +++ | ++ | - | -/+ | - | -/+ | ++ | - | + | - | -/+ |
| Complement lysis | C | +++ | +/- | +/- | -/+ | - | - | + | - | - | - | - |
| ADCC | C | +++ | ++ | +/- | + | - | -/+ | +/- | +/- | + | - | -/+ |
| ADCC | F | ++++ | +++ | + | ++ | + | - | +/- | -/+ | +/- | - | - |

| Inhibition of G1 activity in assay | Series | G1 | G1Δa | G1Δb | G1Δc | G1Δab | G1Δac | G2 | G2Δa | G4 | G4Δb | G4Δc |
|---|---|---|---|---|---|---|---|---|---|---|---|---|
| FcγRI: rosetting | F | | | | | | | | + | | + | |
| FcγRI/II: chemiluminescence | F | | | +++ | ++ | +++ | +++ | + | +++ | | +++ | +++ |
| Complement lysis | C | | | | | | | | + | | | |
| ADCC | F | | - | ++ | + | ++ | ++ | - | + | - | ++ | ++ |

Series  CAMPATH-1 (C) or Fog-1 (F) antibodies tested
++++, +++, ++ or +  relative level of activity in assay
+/-  low level of activity which is significantly above background
-/+  low level of activity which is slightly above background
-  no activity above background
blank  not tested Full C_H2 Sequences of the Parental and Mutated Antibodies

```
                      233      252                               296          310        318       327
                      |234     |253                              |297         |311       |320      |330
                      ||235    ||254                              —           ——        ||322     ||331
                      |||236   ———                                                        ——       ——
                      ————
G1       APELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK
G2       APPVA_GPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK
G3       APEFLGGPSVFLFPPKPKDTLMISRTPEVTCVVVDVSQEDPEVQFKWYVDGVEVHNAKTKPREEQYNSTYRVVSVLTVLHQDWLNGKEYKCKVSNKALPAPIEKTISKTK
G4       APEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAK

G1Δa     APELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK
G1Δb     APPVA_GPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK
G1Δc     APPVAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKOLPSSIEKTISKAK
G1Δab    APPVA_GPSVFLFPPKPKDTLMISRTPEVTCVVVDVSHEDPEVKFNWYVDGVEVHNAKTKPREEQYNSTYRVVSVLTVLHQDWLNGKEYKCKVSNKOLPSSIEKTISKAK
G1Δac    APPVAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKOLPSSIEKTISKAK

Seq ID 1
G2Δa     APPVA_GPSVFLFPPKPKDTLMISRTPEVTCVVVDVSQEDPEVQFNWYVDGVEVHNAKTKPREEQFNSTYRVVSVLTVVHQDWLNGKEYKCKVSNKGLPSSIEKTISKAK

Seq ID 2
G4Δb     APPVA_GPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAK
G4Δc     APPVAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAK
```

Figure 17

BINDING MOLECULES DERIVED FROM IMMUNOGLOBULINS WHICH DO NOT TRIGGER COMPLEMENT MEDIATED LYSIS

This application is a 371 of PCT/GB99/01441 filed May 7, 1999.

TECHNICAL FIELD

The present invention relates to binding polypeptides having amino acid sequences derived from a modified constant region of the immunoglobulin G (IgG) heavy chain. The invention further relates to methods and materials for producing such polypeptides, and methods and materials employing them.

PRIOR ART

Immunoglobulins

Immunoglobulins are glycoproteins which help to defend the host against infection. They generally consist of heavy and light chains, the N-terminal domains of which form a variable or V domain capable of binding antigen. The V domain is associated with a constant or C-terminal domain which defines the class (and sometimes subclass [isotype], and allotype [isoallotype]) of the immunoglobulin.

Thus in mammalian species immunoglobulins exist as IgD, IgG, IgA, IgM and IgE. The IgG class in turn exists as 4 subclasses in humans (IgG1, IgG2, IgG3, IgG4). The C-domain in IgGs comprises three domains Cγ1, Cγ2, and Cγ3, which are very similar between these subclasses (over 90% homology). The Cγ1 and Cγ2 domains are linked by a hinge. The role of the subclasses appears to vary between species.

It is known that the C-domain is responsible for various effector functions of the immunoglobulin (see Clark (1997) "IgG Effector Mechanisms" in "Antibody Engineering" Ed. Capra, Pub. Chem Immunol, Basel, Kurger, Vol 65 pp 88-110, for a detailed review).

Briefly, IgG functions are generally achieved via interaction between the Fc region of the Ig and an Fcγ receptor (FcγR) or other binding molecule, sometimes on an effector cell. This can trigger the effector cells to kill target cells to which the antibodies are bound through their variable (V) regions. Also antibodies directed against soluble antigens might form immune complexes which are targeted to FcγRs which result in the uptake (opsonisation) of the immune complexes or in the triggering of the effector cells and the release of cytokines.

In humans, three classes of FcγR have been characterised, although the situation is further complicated by the occurrence of multiple receptor forms. The three classes are:

(i) FcγRI (CD64) binds monomeric IgG with high affinity and is expressed on macrophages, monocytes, and sometimes neutrophils and eosinophils.

(ii) FcγRII (CD32) binds complexed IgG with medium to low affinity and is widely expressed. These receptors can be divided into two important types, FcγRIIa and FcγRIIb.

The 'a' form of the receptor is found on many cells involved in killing (e.g. macrophages, monocytes, neutrophils) and seems able to activate the killing process, and occurs as two alternative alleles.

The 'b' form seems to play a role in inhibitory processes and is found on B-cells, macrophages and on mast cells and eosinophils. On B-cells it seems to function to suppress further immunoglobulin production and isotype switching to say for example the IgE class. On macrophages, the b form acts to inhibit phagocytosis as mediated through FcγRIIa. On eosinophils and mast cells the b form may help to suppress activation of these cells through IgE binding to its separate receptor.

(iii) FcγRIII (CD16) binds IgG with medium to low affinity and exists as two types. FcγRIIIa is found on NK cells, macrophages, eosinophils and some monocytes and T cells and mediates ADCC. FcγRIIIb is highly expressed on neutrophils. Both types have different allotypic forms.

As well as binding to FcγRs, IgG antibodies can activate complement and this can also result in cell lysis, opsonisation or in cytokine release and inflammation. The Fc region also mediates such properties as the transportation of IgGs to the neonate (via the so-called 'FcRn'); increased half-life (also believed to be effected via an FcRn-type receptor—see Ghetie and Ward (1997) Immunology Today 18, 592-598) and self-aggregation. The Fc-region is also responsible for the interaction with protein A and protein G (which interaction appears to be analogous to the binding of FcRn).

Engineering Immunoglobulins

Many of the Fc-mediated properties discussed above may be desirable in naturally occurring or artificially constructed antibodies. However, there are circumstances where, in particular, the cell killing, or the cytokine release and resulting inflammation, is inappropriate and undesirable.

Equally, however, it may be desirable to retain certain Fc-mediated functions, for instance the long plasma half life.

It is known that human IgG4, for example, does not activate complement and human IgG2 does not bind to the high affinity FcγRI receptor and so these have previously been used in some situations (TNF receptor fusion protein was made with IgG4 Fc).

However no human subclass lacks all of the relevant Fc effector triggering functions or complement activation in all circumstances, possibly owing to the existence of the several forms of the FcγRs. Thus, for instance, IgG4 can trigger antibody dependent cellular cytotoxicity (ADCC) in some people and IgG2 binds to one allelic form of the FcγRIIa receptor and also activates complement.

An alternative approach has been to mutate the Fc sequence to substitute residues crucial for function. Certain target residues have been identified and published (see review by Clark 1997, supra). These include the N-linked carbohydrate attached to the conserved site in the $C_H2$ domain, certain residues in the lower hinge region (eg the sequence ELLGGP (SEQ ID NO:27)) and a proline residue at positions 331 and a sequence E-x-K-x-K at positions 318-322. One recent example is disclosed by Cole et al (1997) Journal of Immunology 159, 3613-3621. In that disclosure residues 234, 235 and 237 were mutated to Alanines (or in the case of 235, sometimes to Glu). However these are all unusual residues at these positions in human IgG, thus the presence of such inappropriate amino acids may make the Fc more immunogenic or antigenic and may also lead to the loss of certain desirable Fc functions.

Again this strategy has been used for the construction of a therapeutic aglycosylated CD3 antibody (see Routledge et al, 1993 Eur J Immunol 23: 403-411; see also UK PA 9206422.9) and for an inhibitory CD18 antibody. However one disadvantage here is that the new recombinant constructs have unusual sequences and may be recognised and rejected by the immune system as foreign. Aglycosylated antibodies also lack binding to the inhibitory receptor FcγRIIb, whereas maintaining this binding may be advantageous for some applications.

Other approaches to modifying immunoglobulins are disclosed in WO 92/16562 (Lynxvale Ltd) which discusses modifying the allotype of the humanised IgG1 antibody CAMPATH1H which has binding affinity for antigen CD52. The CD52 antigen is found on human lymphocytes and monocytes and has been used as a therapeutic target for treatment of T and B-cell lymphomas and leukeamias, immunosuppresion of organ and bone-marrow transplant recipients and also treatment of some autoimmune and related disorders such as rheumatoid arthritis and systemic vasculitis.

WO 95/05468 (Lynxvale Ltd) also disclosed the modification of allotypic determinants in Igs (or derivatives) having desired binding or other effector functions.

It can be seen from the forgoing that the provision of methods or materials which would facilitate the engineering of Fc regions such as to reduce unwanted effects, while retaining or enhancing desirable properties, would provide a contribution to the art.

DISCLOSURE OF THE INVENTION

The present inventors have used novel combinations of human IgG subclass sequences to generate chimaeric polypeptides comprising non-natural, human-mimicing Fc sequences which nevertheless do not activate complement or trigger cytotoxic activities through FcγR. At the same time certain desirable IgG properties have been retained. For instance the polypeptides do not contain 'non-human' amino acids, and are therefore likely to have reduced immunogenicity. Further, they still bind Protein A, which is consistent with being able to cross the human placenta through interaction with FcRn (neonatal Fc receptor).

The manner by which the sequences were developed, and certain demonstrated properties, will be discussed in more detail hereinafter. However, briefly, the inventors formulated numerous constructs based on three different IgG sequences (1, 2 and 4). Although the relevant regions of these antibodies share homology, they do not precisely correspond in terms of length, thereby complicating the process of generating derivative sequences which retain activities from the natural sequences. The constructed antibodies were compared with the parental control antibodies in the context of model antigen systems RhD (Fog1) and CD52 (CAMPATH-1H). Surprisingly, a number of sequences were developed with the required combination of activities not found in the parent molecules. Generally speaking these contained 1 or more regions or blocks which contained a modification (generally 2, 3 or 4 amino acids) which was in conformity with the corresponding region from a different subclass. Two particular regions or blocks of interest were 233-236 and 327,330, 331.

Thus in a first aspect of the present invention there is disclosed a polypeptide binding molecule comprising (i) a binding domain capable of binding a target molecule, and (ii) an effector domain having an amino acid sequence substantially homologous to all or part of a constant domain of a human immunoglobulin heavy chain; characterised in that the binding molecule is capable of binding the target molecule without triggering significant complement dependent lysis, or cell mediated destruction of the target, and preferably whereby the effector domain is capable of specifically binding FcRn or FcγRIIb, more preferably both FcRn and FcγRIIb.

The specific binding of FcRn may be evidenced by the capability to specifically bind protein A.

Thus the binding molecules according to the present invention have improved clinical properties (e.g. in the context of 'blocking' antibodies). This is achieved by the provision of an Fc-derived effector domain which has a reduced affinity for FcγRI, FcγRIIa and FcγRIII, but which retains the ability to bind protein A (and hence FcRn, hence permitting neonatal transport and high half life) and/or FcγRIIb. Thus the residues responsible for binding FcRn in IgGs need not be modified with respect to a natural Fc region in the molecules of the present invention.

Generally the reduction in affinity which the effector region has for the receptor FcγRI (as compared with one Fc region from which it is derived) may, in preferred embodiments, be of the order of 100 fold or more. For certain of the lower affinity receptors discussed above the reduction in affinity may be less e.g. around 2-10 fold, although in the most preferred embodiments it could be as high 500 fold. Generally the corresponding reduction in activity in the chemiluminescence assay (as described in more detail below) may be as high as 30-300 fold. The reduced complement activity may be of the order of 50 fold. The corresponding figure for ADCC may be much higher e.g. 10,000 fold. However those skilled in the art will appreciate that the combination of these (reduced) activities may still be of benefit in certain applications, regardless of the precise level of reduction.

Although IgG1/IgG2 and IgG1/IgG4 chimeras have been prepared in the past (see e.g. Morgan et al (1995) Immunology 86: 319-324, or Chappel et al (1991) Proc Natl Acad Sci USA 88: 9036-9040, or Greenwood et al (1993) Eur J Immunol 23: 1098-1104) none of these has been shown to have the combination of properties possessed by the binding molecules of the present invention.

The various functions of the binding molecule can be assessed without burden by those skilled in the art, for instance by using methods as disclosed below, or methods analogous to these. For instance, the FcγR binding properties may be assessed directly, or indirectly e.g. through inability to trigger monocyte chemiluminescence.

Specifically, the inability to trigger significant complement dependent lysis (which will generally be through a reduced affinity for the C1q molecule) can be measured by CR-51 release from target cells in the presence of the complement components e.g. in the form of serum (as described below) whereby the binding molecule causes less than 5%, preferably less than 2% specific target cell lysis.

Similarly, cell mediated destruction of the target may be assessed by CR-51 release from target cells in the presence of suitable cytotoxic cells e.g. blood mononuclear effector cells (as described below) whereby the binding molecule causes less than 5%, preferably less than 2% target cell lysis.

As an alternative to direct measurement, functionality may be inferred by the ability to inhibit these attributes in functional immunoglobulins. For instance by providing a protective effect against the complement lysis of cells, or the killing of cells (e.g. by ADCC), or by inhibiting the response of monocytes to sensitised cells.

In one, preferred, embodiment of this aspect of the invention the effector domain comprises an amino acid sequence substantially homologous to the $C_H2$ sequence from human IgG1, G2 or G4, said sequence comprising one or more of the following modifications (amino acid substitutions or deletions) at the stated positions, numbered with respect to the EU numbering system (see Kabat et al "Sequences of proteins of immunological interest". Bethesda, US Department of Health and Human Services, NIH, 1991):

| Posn | Amino acid |
| --- | --- |
| 233 | P |
| 234 | V |
| 235 | A |
| 236 | (No residue) or G |
| 327 | G |
| 330 | S |
| 331 | S |

In a preferred embodiment, these substitutions are made in 'blocks' of 233-236 and/or 327,330,331. Thus the mutated region in the $C_H2$ domain will be 100% homologous to the subclass from which the substituted residues originated, thereby reducing the likelihood that the region will represent a B-cell or T-cell epitope for the immune system.

Several mutant immunoglobulins based on IgG1, IgG2, or IgG4 having the stated features, have been prepared and have shown to have the required properties. Although some of the individual residue mutations have been prepared in binding molecules of the prior art, the specified combinations are novel as are the achieved functionalities.

Preferred forms of the binding molecule will now be discussed in more detail:

The Effector Domain

The peptide comprises an effector domain having an amino acid sequence substantially homologous to all or part of a human immunoglobulin constant region, preferably an IgG C-domain.

Numerous sequences for human C regions have been published; see e.g. Clark (1997) supra. Other sequences for human immunoglobulin heavy chains can be obtained from the SwissProt and PIR databases using Lasergene software (DNAStar Limited, London UK) under accession numbers A93433, B90563, A90564, B91668, A91723 and A02146 for human Igγ-1 chain C region, A93906, A92809, A90752, A93132, A02148 for human Igγ-2 chain C region, A90933, A90249, A02150 for human Igγ-4 chain C region, and A23511 for human Igγ-3 chain C region.

Homology (or identity, or similarity) may be assessed by any convenient method. Homology may be at the encoding nucleotide sequence or encoded amino acid sequence level. By "substantially homologous" is meant that the comprised amino acid sequence shares at least about 50%, or 60%, or 70%, or 80% homology, most preferably at least about 90%, 95%, 96%, 97%, 98% or 99% homology with the reference immunoglobulin.

Similarity or homology may be as defined and determined by the TBLASTN program, of Altschul et al. (1990) *J. Mol. Biol.* 215: 403-10, which is in standard use in the art, or, and this may be preferred, the standard program BestFit, which is part of the Wisconsin Package, Version 8, September 1994, (Genetics Computer Group, 575 Science Drive, Madison, Wis., USA, Wisconsin 53711). BestFit makes an optimal alignment of the best segment of similarity between two sequences. Optimal alignments are found by inserting gaps to maximize the number of matches using the local homology algorithm of Smith and Waterman.

This assessment can be made without burden by a person of ordinary skill in the art, in conjunction with assessing the required combination of activities, in order to recognise a molecule of the present invention.

In addition to having the reduced affinity for FcγRI, FcγRIIa FcγRIIIa and FcγRIIIb, it may be desirable that an ability to bind the 'inhibitory' receptor FcγRIIb is retained or possessed to some degree by the effector molecule, and preferably is higher than its affinity for the FcγRIIa receptor, and more preferably commensurate with that of a parent Ig domain from which it is derived. Results obtained by the present inventors indicate that the binding molecules which they have developed do have this property. Hitherto it was not appreciated in the art that the binding of Fc regions to FcγRIIa and FcγRIIb could be manipulated independently. This ability may complement the other required functions (as indicated by the ability to bind protein A) in increasing the therapeutic potential of the binding molecule.

In particular, a number of publications have highlighted the important role that FcγRIIb may play in inhibiting cellular processes (see Daeron et al, 1995 Immunity 3(5): 635-46; Van den Herik et al, 1995 Blood 85(8): 2201-11; Sarmay et al, 1996 Immunol Lett 54(2-3): 93-100; Fong et al, 1996 Immunol Lett 54(2-3): 83-91; Sarmay et al, 1996 J Biol Chem 271(48): 30499-504; Unkeless & Jin, 1997 Curr Opin Immunol 9(3): 338-43; Isakov, 1997 Immunol Res 16(1): 85-100; Hunter et al, 1998 Blood 91(5): 1762-8; Malbec et al, 1998 J Immunol 160(4): 1647-58; Clynes et al, 1999 J Exp Med 189(1): 179-85). These workers showed that FcγRIIb, when cross-linked to other receptors, could inhibit signalling from them, thereby inhibiting such processes as B cell activation, mast cell degranulation, and phagocytosis by macrophages.

Thus binding molecules of the present invention which retain this activity could be used not only to compete with, and competitively inhibit, undesirable antibody-antigen (such as autoantigens or alloantigens) interactions, but also to non-competitively inhibit these processes e.g. by preventing further autoantibody or alloantibody production by inhibition of B cell activation. Other example applications for this inhibitory effect are discussed below in relation to allergy and asthma therapeutics (inhibition of mast cell degranulation) and anti-RhD molecules (inhibition of phagocytosis).

Preferably the effector domain is itself derived from a human immunoglobulin constant region, more preferably an IgG C-domain.

Preferably the comprised amino acid sequence is substantially homologous to the $C_H2$ sequence (i.e. approximately residues 231-340) from human IgG1, G2 or G4, having the modified amino acids discussed above.

The most preferred $C_H2$ sequences are shown in FIG. 17, particularly those designated G1Δab, G2Δa, or G1Δac respectively.

Any of these sequences may be combined with (e.g run contiguously with) natural or modified $C_H3$ and natural or modified hinge region, plus optionally $C_H1$, sequences in the molecules of the present invention.

However it will be appreciated by those skilled in the art that there is no requirement that other portions of the effector domain (or other domains of the molecule) comprise natural sequences—in particular it may be desirable to combine the sequence modifications disclosed herein with others, for instance selected from the literature, provided only that the required activities are retained. The skilled person will appreciate that binding molecules comprising such additionally-modified (e.g by way of amino acid addition, insertion, deletion or substitution) effector domains fall within the scope of the present invention.

Particularly preferred may be 'null allotype' sequences, such as IgG heavy chain-derived sequences (see WO 92/16562) wherein allotypic residues are mutated to match those found in other human IgG subclass molecules. This may minimise the sequences being viewed as foreign by any individual.

The Binding Domain and Target Molecule

The peptide molecule comprises a binding domain capable of binding a target molecule.

The binding domain will have an ability to interact with a target molecule which will preferably be another polypeptide, but may be any target (e.g. carbohydrate, lipid (such as phospholipid) or nucleic acid). Preferably the interaction will be specific. The binding domain may derive from the same source or a different source to the effector domain.

For instance, while the effector domain will generally derive from an antibody, the binding domain may derive from any molecule with specificity for another molecule e.g. an enzyme, a hormone, a receptor (cell-bound or circulating) a cytokine or an antigen (which specifically binds an antibody).

Preferably, it comprises all or part of an antibody or a derivative thereof, particularly a natural or modified variable domain of an antibody. Thus a binding molecule according to the present invention may provide a rodent or camelidae (see WO 94/25591) originating antibody binding domain and a human immunoglobulin heavy chain as discussed above.

Also preferred may be molecules having more than one type of binding domain, such as bispecific antibodies (see e.g. PCT/US92/09965). In these cases one 'arm' binds to a target cell and the other binds to a second cell to trigger killing of the target. In such cases it may be desirable to minimise the impact the effector portion, which might otherwise activate further cells which interfere with the desired outcome. The 'arms' themselves (i.e. the binding domain) may be based on Ig domains (e.g. Fab) or be from other proteins as in a fusion protein, as discussed in more detail below.

The binding molecule may comprise more than one polypeptide chain in association e.g. covalent or otherwise (e.g. hydrophobic interaction, ionic interaction, or linked via sulphide bridges). For instance it may comprise a light chain in conjunction with a heavy chain comprises the effector domain. Any appropriate light chain may be used e.g. the most common kappa light chain allotype is Km(3) in the general population. Therefore it may be desirable to utilise this common kappa light chain allotype, as relatively few members of the population would see it as foreign.

Typically the target will be an antigen present on a cell, or a receptor with a soluble ligand for which the antibody competes.

This may be selected as being a therapeutic target, whereby it is desired to bind it with a molecule having the properties discussed above, for instance to compete with or displace undesirable antibodies from it. Alternatively it may be desirable per se to bind the target molecule, without causing cell mediated destruction, antibody triggered inflammation or complement lysis. Equally the effector domain may function primarily in mediating transport and/or improved serum half life—in such cases the binding domain and target molecule may be any system which would benefit from these qualities.

A selection of applications wherein binding molecules of the present invention could be used as therapeutic antibodies having inert (in some respects) Fc regions are set out below:

1) Competition with Maternal IgG Alloantibodies for Antigenic Epitope on Blood Cells of Fetus/Neonate Alloimmune disorders of fetal blood cells have a common pathogenesis. There is synthesis of IgG alloantibodies by the mother to a paternally inherited antigen on fetal red cells, granulocytes or platelets. This is followed by transplacental transport of the alloantibody. In the fetus or neonate, there is destruction of antibody-coated fetal blood cells, which may lead to a clinically significant fall in circulating levels of the relevant cells. Therapeutic antibodies to the relevant epitope, but with an Fc which does not trigger destruction, could compete with maternal antibody for binding to fetal cells, thus inhibiting their destruction.

Antibodies to Red Cell Alloantigens Lead to Haemolytic Disease of the Fetus and Neonate The most important red cell alloantigens are in the Rhesus and Kell blood group systems. The incidence of haemolytic disease due to the RhD antigen has fallen dramatically since the introduction of post-natal prophylaxis, but cases still occur due to maternal sensitisation during the first pregnancy. Other Rhesus antigens (C,c,E,e) can also cause haemolytic disease, as can antibodies to the Kell (Kl) antigen, which in addition impair erythopoiesis in the fetal bone marrow.

Current therapy for severely affected fetuses consists of regular intra-uterine transfusion of antigen negative red cells. Infusions of non-specific immunoglobulin have not been shown to be effective in this condition. Anaemia and hyperbilirubinaemia in the neonate may require exchange transfusion and/or phototherapy.

Experiments using inert Fc constructs with RhD specificity (designated Fog-1) have demonstrated their failure to trigger effector mechanisms (monocyte activation as detected by chemiluminescence and ADCC), and importantly have also been shown to inhibit chemiluminescence and ADCC triggered by human sera containing polyclonal anti-D. ADCC and chemiluminescence have previously been shown to predict red cell destruction in vivo. Previously published work has also demonstrated the ability of Fog-1 to compete with the majority of human anti-D sera for epitopes on the RhD protein.

Antibodies to Platelet Alloantigens Lead to Fetal and Neonatal Alloimmune Thrombocytopenia The most relevant antigen is human platelet antigen (HPA)-1a. HPA-1a antibodies complicate 1 in 350 normal pregnancies, and lead to severe thrombocytopenia in 1 in 1200 fetuses. The most severely affected cases result in intracranial haemorrhage or death. The current options for therapy are weekly transfusions of HPA-1a negative platelets (which carries a risk of fetal death of 0.5%/procedure), and high dose intravenous immunoglobulin given to the mother, which has variable and unpredictable efficacy. HPA-1a is defined by a single epitope on platelet glycoprotein IIIa (GPIIIa), and a single chain Fv recognising this epitope is available within the University of Cambridge Division of Transfusion Medicine (Griffin H M, Ouwehand W H. A human monoclonal antibody specific for the Leucine-33 ($PA^{A1}$, HPA-1a) form of platelet glycoprotein IIIa from a V gene phage display library. Blood 1995; 86: 4430-4436). The binding of an antibody based on this construct to human platelets has been shown to be inhibited by human anti-HPA-1a-sera. The inhibition was most consistent for sera with the highest titre of specific antibodies, which were associated with the most severe disease. This indicates that the recombinant antibody and sera antibodies bind to the same epitope on platelets.

In the above applications, and those below, in addition to a competitive binding effect, the therapeutic antibodies of the present invention may also trigger a beneficial inhibitory effect through FcγRIIb.

2) Competition With Autoantibody For Epitope on Autoantigen

Autoantibody Mediated Blood Cell Destruction

Haemolytic anemia by warm type IgG autoantibodies and thrombocytopenia by autoantibodies have a common mechanism of blood cell destruction. In both, autoantibodies target a selected repertoire of autoantigens (Rh and K on red cells, and GPIIb/IIIa,GPIb/IX/V on platelets). The binding of the autoantibody shortens the life-span of the blood cell leading to anemia or thrombocytopenia, respectively. It is not unlikely that red cell and platelet autoantibodies target a limited number of B-cell epitopes on their respective autoantigens. Recombinant variable domain antibodies against these epitopes can be generated by V gene phage display technology. Therapeutic antibodies to the relevant epitopes, but with inert Fc, could compete with the patient's blood cell autoantibodies for binding to the autoantigen, thus inhibiting the destruction of the blood cell.

Goodpasture's Syndrome (Anti-Glomerular Basement Membrane [GBM] Disease)

This is a major cause of rapidly progressive glomerulonephritis, leading to lung haemorrhage and end-stage renal failure in weeks or months from onset. Conventional therapy depends on dialysis in combination with intensive plasma exchange and immunosuppressive therapy, which in itself may be complicated by life-threatening opportunistic fungal and viral infections. There is overwhelming evidence that this disease is mediated by autoantibodies, and the autoantigen has been localised to type IV collagen, a major component of GBM. It has been shown that autoantibodies in GBM disease bind to the non-collagenous (NC1) domain of the α3 (IV)-chain. The gene encoding this sequence (COL4A3) has been cloned and sequenced. We hypothesise that the effect of harmful anti-GBM autoantibodies can be neutralised by a monoclonal IgG competitor molecule which targets the immundominant epitope on α3 (IV)NC1 and has, by design, been equipped with a biologically inactive Fc domain. We will develop a recombinant chimaeric IgG antibody which binds the immunodominant α3 (IV)NC1 epitope but that lacks the classic effector functions. We will be able to achieve this as the genes encoding the variable domains of the murine anti-α3 (IV)NC1 have been developed and characterised (Pusey C D et al, Lab Invest 1987, 56;23-31 and Ross C N et al, Lab Invest 1996, 74;1051-1059).

Once again, in addition to a competitive binding effect, the therapeutic antibodies of the present invention may also trigger a beneficial inhibitory effect through FcγRIIb.

3) Allergy and Asthma

Allergies and asthma result from innappropriate immune responses to common environmental antigens such as proteins from grass pollens, house dust mites and many other common antigen sources, an example being the Der P 1 protein of the house dust mite *Dermatophagoides pteronyssinus*. Affected individuals make high levels of immunoglobulins particularly of the IgE class. These IgE antibodies are able to bind to the high affinity Fc-epsilon RI receptor on Mast cells and on Eosinophils. Cross-linking of the receptor bound IgE by the allergen results in activation of the cells and degranulation. This releases a number of inflammatory mediators which can cause severe symptoms or even death as a result of an anaphylactic reaction. Two mechanisms of action of a blocking antibody could be envisaged. Firstly an IgG antibody with an inert Fc region could compete for the binding of allergen to IgE. This would prevent the cross-linking of IgE and hence prevent the activation of the cells. For this mechanism the IgG antibody with inert Fc would have to compete directly for the binding of the allergen with the IgE.

A second, significant, mechanism would involve the role of negative signalling through the FcγRIIb receptor. It has been shown that the cross-linking of Fc gamma RIIB and Fc epsilon RI results in an inhibition of the activation signals normally seen when only Fc epsilon RI receptors are cross-linked. Thus the introduction of an IgG antibody with an Fc binding capacity for Fc gamma RIIb and an antigen specificity for an allergen could result in a an inhibition of the activation of IgE coated Mast cells and Eosinophils. For this the IgG antibody would also mediate its strong negative affect if it bound the allergen by a different site to the IgE such that both could bind to the allergen at the same time.

4) Inflammatory Disorders eg. Crohn's Disease

There are a number of disorders of the immune system which seem to cause pathology as a result of the chronic state of activation of immune cells (leukocytes), including T-lymphocytes, neutrophils and NK-cells. This chronic activation is normally seen as a state of inflammation with a continued migration of activated cells into the tissues affected. In order to migrate into the tissue the cells must receive and respond to inflammatory mediators and then regulate adhesion molecules to enable them to first adhere to the cells lining the blood vessel walls and then to migrate between the cells of the vessel walls and into the tissue. It should be possible to stop this cycle of inflammation by either blocking the adhesion molecules on the surface of the leukocytes or the corresponding ligands on the activated epithelial cells lining the vessel walls. Such an activation antigen is VAP-1 and an antibody with an inert Fc which binds to this molecule should prevent leukocyte adherance and migration at sites of the inflammation thus breaking the cycle of chronic activation.

5) Inhibition of Ligand/Receptor Interaction

Sickle Cell Disease

Homozygosity for the variant of human haemoglobin characterised by a substitution of valine for glutamic acid (HbSS) leads to chronic haemolysis and a tendency for the molecule to undergo tactoid formation in the deoxygenated state. This leads to the red cells adopting a sickle shape in the microcirculation leading to sickle 'crises' in localised areas. These may be thrombotic (in bone, lung, brain or abdomen), aplastic, haemolytic or associated with massive red cell sequestration in spleen and liver. It is postulated that during these crises red cells adhere to endothelial cells. This process of adhesion is based on the interaction of several receptor with their respective ligands. Two of the dominant adhesion pathways are the interaction between Lutheran and laminin and between thrombospondin and an as yet undefined red cell membrane lipid. In animal experiments we have obtained evidence that recombinant human variable domain antibodies against thrombospondin diminish the adhesion of sickling red blood cells to endothelial cells. We postulate that similar recombinant variable domain antibodies against the laminin binding domain of lutheran (the membrane proximal domain) which block the interaction with laminin can be developed by V gene phage display. These variable domain antibody fragments can be equipped with inert Fc domains to produce therapeutic antibodies able to interfere with the adherence of sickling red blood cells to endothelial cells, without causing red cell destruction.

Antibody Mediated Blocking of Platelet Collagen Receptors

We have substantial evidence that two receptors are crucial to platelet activation by subendothelial collagens, an event initiating thrombosis; the integrin $\alpha_2\beta_1$ (platelet glycoprotein Ia/IIa) which we view primarily as adhesive in function, and the non-integrin glycoprotein VI (GpVI) as essential for activation, preceding secretion and aggregation. Recombinant human antibodies may be generated by V gene phage display recognising different domains within each receptor, and these may be used to produce lead-antibodies with an inert Fc domain for collagen-based anti-thrombotic therapy. These may be used in the alleviation of coronary thrombosis, of restenosis after angioplasty and of thrombotic complications associated with bypass grafting.

6) Monoclonal antibodies are used sometimes to block cell functions, eg OKT3 is used to immunosuppress T-cells by blocking the T-cell receptor and CD18 antibodies are used to prevent cell-cell adhesion through the integrin molecules. However the binding of the Fc to Fc receptors can trigger serious side effects through stimulating cytokine release and inflammation.

7) Antibody Fc regions are sometimes attached to other recombinant proteins to give fusion molecules with prolonged biological half-lives. Thus TNF receptor has been attached to human IgG4 Fc to form a molecule which inhibits the effects of soluble TNF, and CTLA4 has been made as a fusion protein with IgG Fc and used to block signalling through the B7 coreceptor (a ligand for CTLA4) molecule on cell surfaces. However again cytokine triggering by the Fc of the fusion protein is undesirable.

V domains, or other binding regions, appropriate to the types of application discussed above, where discussed specifically, will be well known to those skilled in the art. For instance a CD3 binding domain (e.g. YTH12.5) is disclosed by Routledge et al (1991) Eur J Immunol 21, 2717-2725 and Bolt et al (1993) Eur J Immunol 23, 403-411. A CD52 binding domain (e.g. CAMPATH-1) is disclosed by Riechmann et al (1988) Nature 332, 323-327. A VAP-1 binding domain is disclosed by Salmi et al (1993) J Exp Med 178:2250-60 and Smith et al (1998) J Exp Med 188: 17-27. A Der p I domain (e.g. 2C7) is disclosed by McElveen et al (1998) Clin Exp Allergy 28, 1427-1434.

Thus a binding molecule which did not bind to Fc receptors and trigger killing, and did not activate complement, but which did bind to a target molecule, could be used in all of the above examples to minimise any side effects. Specifically, such a 'blocking' antibody could be introduced in situations 1-5 above and prevent the undesirable destruction by the naturally occurring antibodies. The same blocking type Fc regions would be the Fc regions of choice to use for recombinant antibodies such as the CD3 or CD18 antibodies in 6 above or as the Fc for fusions in 7 above.

The binding and effector domains may be combined by any suitable method. For instance domains may be linked covalently through side chains. Alternatively, sulphydryl groups generated by the chemical reduction of cysteine residues have been used to cross-link antibody domains (Rhind, S K (1990) EP 0385601 Cross-linked antibodies and processes for their preparation). Finally, chemical modification of carbohydrate groups has been used to generate reactive groups for cross-linking purposes. These methods are standard techniques available to those skilled in the art. They may be particularly applicable in embodiments wherein the binding polypeptide contains non-protein portions or groups.

Generally it may be more appropriate to use recombinant techniques to express the binding molecule in the form of a fusion protein. Methods and materials employing this approach form further aspects of the present invention, as set out below.

Nucleic Acids

In one aspect of the present invention there is disclosed a nucleic acid encoding a binding molecule as described above.

Nucleic acid according to the present invention may include cDNA, RNA, genomic DNA (including introns) and modified nucleic acids or nucleic acid analogs (e.g. peptide nucleic acid). Where a DNA sequence is specified, e.g. with reference to a Figure, unless context requires otherwise the RNA equivalent, with U substituted for T where it occurs, is encompassed.

Nucleic acid molecules according to the present invention may be provided isolated and/or purified from their natural environment, in substantially pure or homogeneous form, or free or substantially free of other nucleic acids of the species of origin. Where used herein, the term "isolated" encompasses all of these possibilities.

The nucleic acid molecules may be wholly or partially synthetic. In particular they may be recombinant in that nucleic acid sequences which are not found together in nature (do not run contiguously) have been ligated or otherwise combined artificially. Alternatively they may have been synthesised directly e.g. using an automated synthesiser.

In a further aspect there is disclosed a nucleic construct, e.g. a replicable vector, comprising the nucleic acid sequence.

A vector including nucleic acid according to the present invention need not include a promoter or other regulatory sequence, particularly if the vector is to be used to introduce the nucleic acid into cells for recombination into the genome.

Preferably the nucleic acid in the vector is under the control of, and operably linked to, an appropriate promoter or other regulatory elements for transcription in a host cell such as a microbial, (e.g. bacterial, yeast, filamentous fungal) or eucaryotic (e.g. insect, plant, mammalian) cell.

Particularly, the vector may contain a gene (e.g. gpt) to allow selection in a host or of a host cell, and one or more enhancers appropriate to the host.

The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

By "promoter" is meant a sequence of nucleotides from which transcription may be initiated of DNA operably linked downstream (i.e. in the 3' direction on the sense strand of double-stranded DNA). The promoter may optionally be an inducible promoter.

"Operably linked" means joined as part of the same nucleic acid molecule, suitably positioned and oriented for transcription to be initiated from the promoter. DNA operably linked to a promoter is "under transcriptional initiation regulation" of the promoter. Thus this aspect of the invention provides a gene construct, preferably a replicable vector, comprising a promoter operatively linked to a nucleotide sequence provided by the present invention.

Generally speaking, those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press.

Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference.

Host Cells & Methods

Also embraced by the present invention are cells transformed by expression vectors defined above. Also provided are cell cultures (preferably rodent) and products of cell cultures containing the binding molecules.

Also provided are methods of making binding molecules according to the present invention comprising:
(i) combining a nucleic acid encoding a binding domain with a nucleic acid encoding an effector domain to form a nucleic acid construct;
(ii) causing or allowing the expression of the construct in a suitable host cell.

Combination, to produce a construct, can be by any convenient method known to those skilled in the art, for instance by ligation of fragments (e.g. restriction fragments) or using different templates in one or more amplification steps e.g. using PCR.

Methods of producing antibodies (and hence binding domains) include immunising a mammal (e.g. human, mouse, rat, rabbit, horse, goat, sheep, camel or monkey) with a suitable target protein or a fragment thereof. Antibodies may be obtained from immunised animals using any of a variety of techniques known in the art, and might be screened, preferably using binding of antibody to antigen of interest.

For instance, Western blotting techniques or immunoprecipitation may be used (Armitage et al, 1992, Nature 357: 80-82).

Cloning and expression of Chimaeric antibodies is described in EP-A-0120694 and EP-A-0125023.

The nucleic acid encoding the effector domain can be generated, in the light of the present disclosure, by site directed mutagenesis, for instance by methods disclosed herein or in the published art (see e.g. WO 92/16562 or WO 95/05468 both of Lynxvale Ltd).

Other Aspects

Also provided is use of the binding molecules of the present invention to prevent, inhibit, or otherwise interfere with the binding of a second binding molecule to a target molecule. This may involve competing with, or displacing, an antibody from a therapeutically relevant target antigen or cell.

The present invention also provides a reagent which comprises a binding molecule as above, whether produced recombinantly or otherwise.

The present invention also provides a pharmaceutical preparation which comprises a binding molecule as above, plus a pharmaceutically acceptable carrier.

The present invention also provides a method of treating a patient which comprises administering a pharmaceutical preparation as above to the patient, or to a sample (e.g. a blood sample) removed from that patient, which is subsequently returned to the patient. Particularly a method of treatment for the following diseases: Graft-vs-host disease; host-vs-graft disease; organ transplant rejection; bone-marrow transplant rejection; autoimmunity; alloimmunity; allergy; chronic or acute inflammatory diseases.

The present invention also provides a method of treating a patient which comprises causing or allowing the expression of a nucleic acid encoding a binding molecule as described above, whereby the binding molecule exerts its effects in vivo in the patient. Generally the expression will occur in the patient, or in certain specialised circumstances where the patient is an unborn infant, in the mother of the patient.

Also provided is the use of a binding molecule as above in the preparation of a pharmaceutical to modify an immune response, particularly a pharmaceutical for the treatment of the diseases discussed above.

In order that the present invention is more fully understood embodiments will now be described in more detail, by way of example only, and not by way of limitation. Other embodiments falling within the scope of the invention may occur to those skilled in the art in the light of these.

FIGURES

FIG. 1 Rosetting of FcγRI-bearing cells by RBC coated with Fog-1 antibodies. $R_2R_2$ RBC were coated with Fog-1 antibodies at a range of antibody concentrations, incubated with B2KA cells growing in a 96-well plate and the percentage of B2KA cells with rosettes of RBC determined. Error bars indicate the standard deviation values for triplicate wells. For the mutants Fog-1 G1Δb, G1Δc, G1Δab, G1Δac, G2Δa, G4Δb and G4Δc, as for G2 (shown), there was no rosetting between B2KA cells and RBC at any of the coating concentrations.

Figure 2:
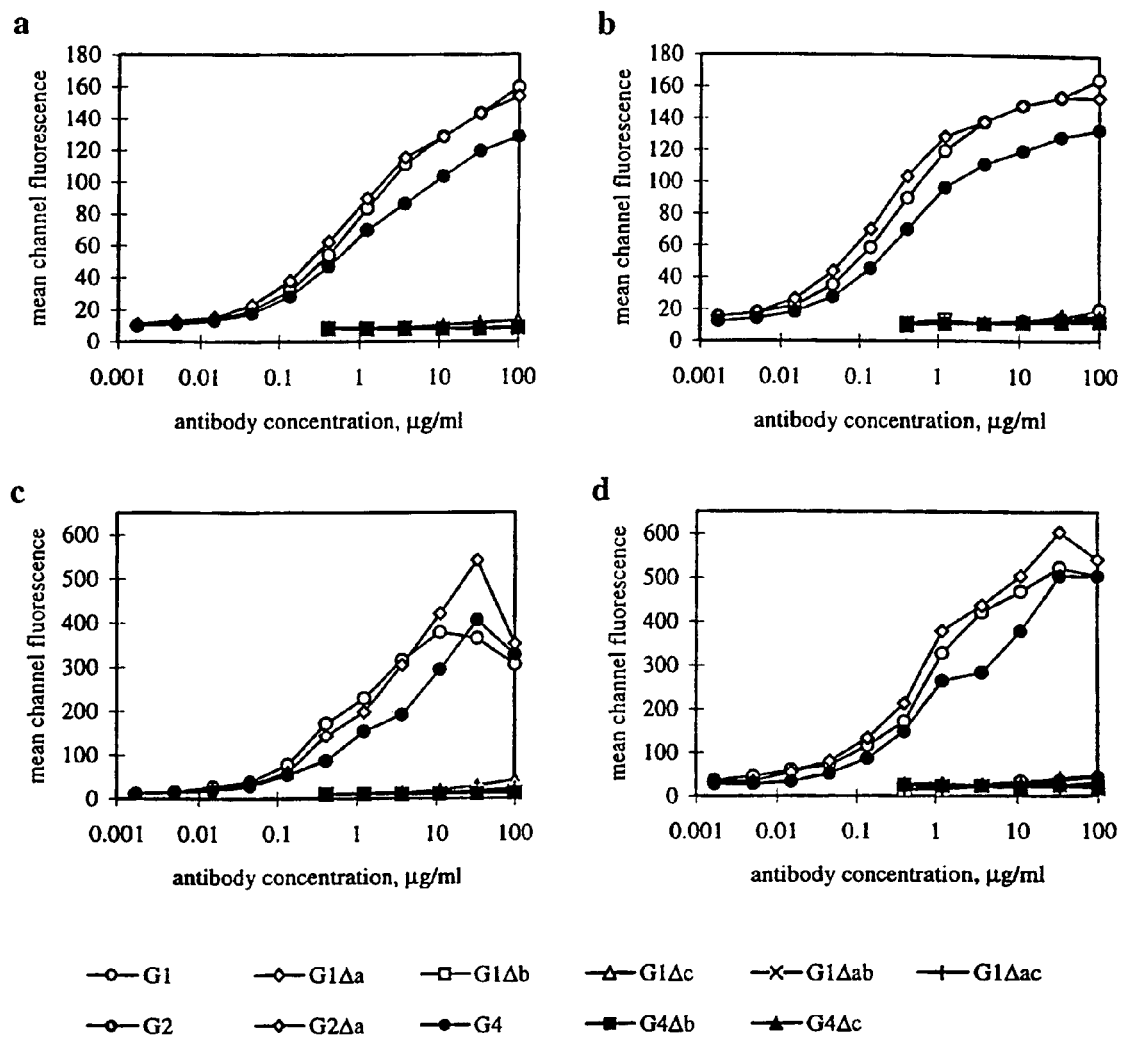

FIG. 2 Fluorescent staining of FcγRI-bearing cells. FcγRI transfectant cell lines, B2KA(a and b) and 3T3+FcγRI+γ-chain (c and d) were incubated sequentially with antibodies of the CAMPATH-1 (a and c) or Fog-1 (b and d) series, biotinylated anti-human K antibodies and ExtrAvidin-FITC. The fluorescence intensities were measured for 10000 events and the geometric mean channel of fluorescence plotted.

Figure 3:
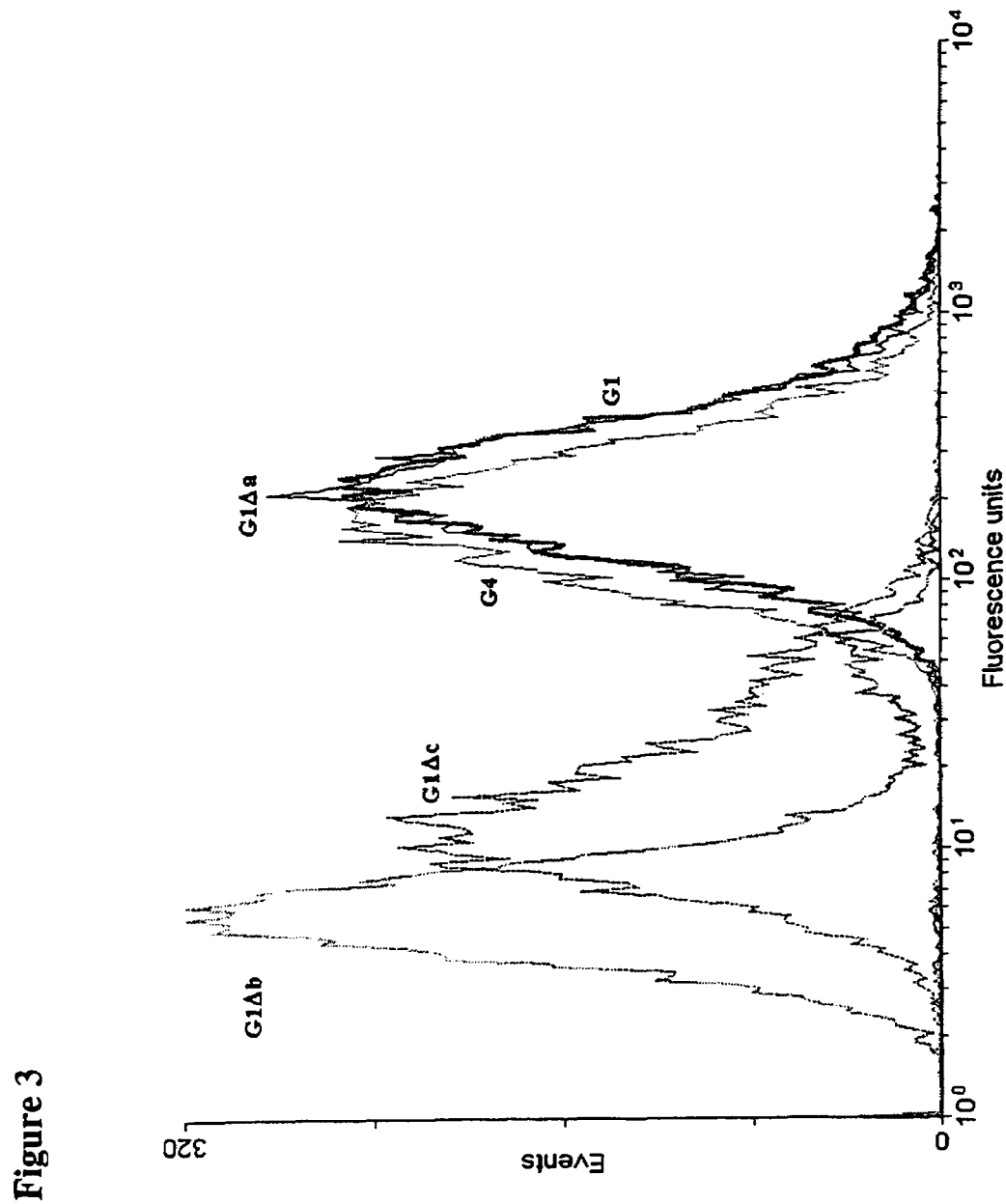

FIG. 3 Histogram representation of fluorescently stained FcγRI-bearing cells. B2KA cells were stained as in FIG. 2 using 100 μg/ml antibodies from the CAMPATH-1 series. The histogram plots showing the number of cells falling in each fluorescence channel were overlaid for representative antibodies.

Figure 4:
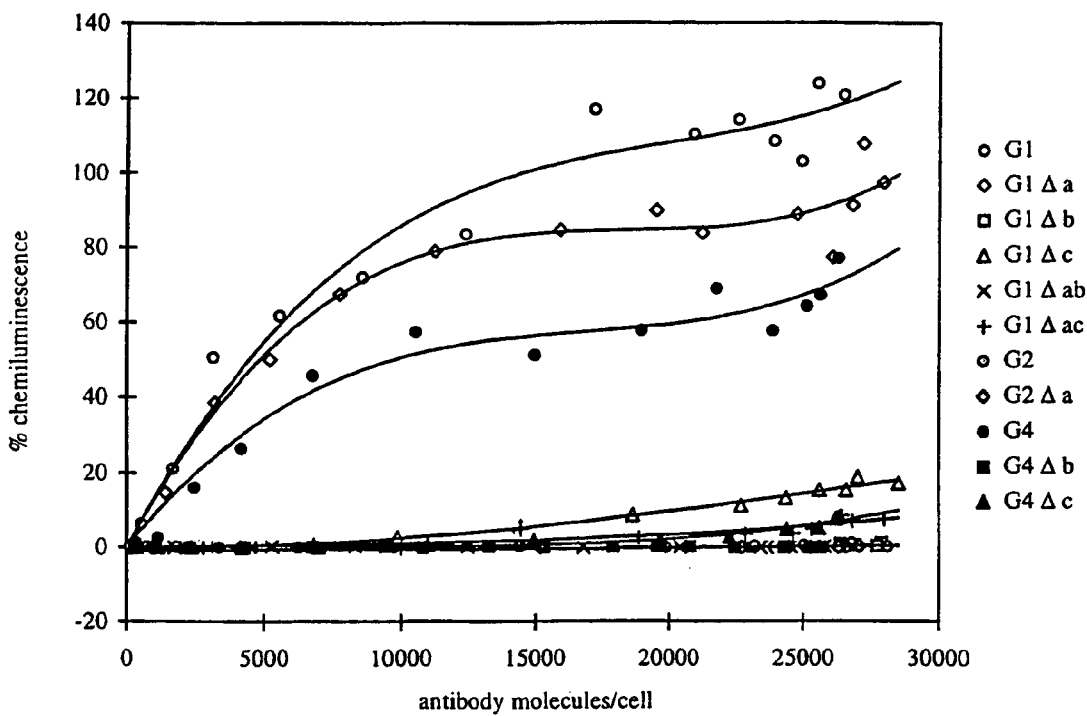

FIG. 4 CL response of human monocytes to RBC sensitized with Fog-1 series of antibodies. $R_1R_1$ RBC were coated with antibodies over a range of concentrations. The number of antibody molecules bound per cell and the CL response of moncytes to the RBC was determined for each sample as described.

Figure 5:
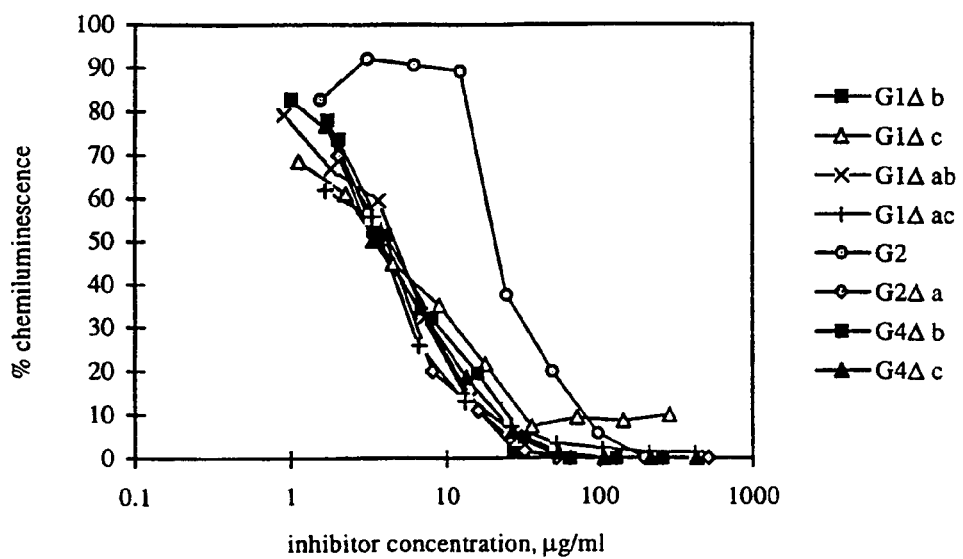

FIG. 5 Inhibition of CL due to Fog-1 G1 by other Fog-1 antibodies. RBC were sensitized with 2 μg/ml Fog-1 G1 and different concentrations of the Fog-1 Ab indicated. These Ab gave a low CL response in FIG. 4. The CL response of monocytes was measured. The response due to 2 μg/ml G1 alone is taken as 100%.

Figure 6:
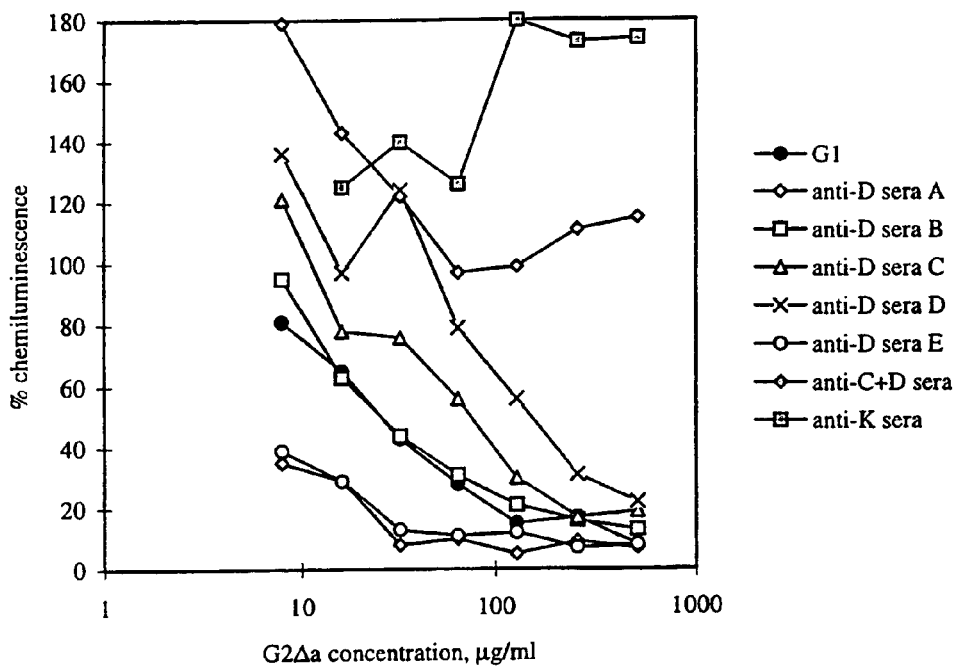

FIG. 6 Inhibition of CL response to clinical sera by Fog-1 G2Δa. RBC were sensitized with a constant amount of Fog-1 G1 (20 μg/ml) or clinically relevant sera and different amounts of Fog-1 G2Δa. 100% response was achieved with a standard amount of BRAD 5. In the absence of Fog-1 G2Δa, the % responses were G1: 150%, sera A: 142%, sera B: 265%, sera C: 200%, sera D: 163%, sera E: 94%, anti-C+D sera: 259% and anti-K sera: 119%.

Figure 7:
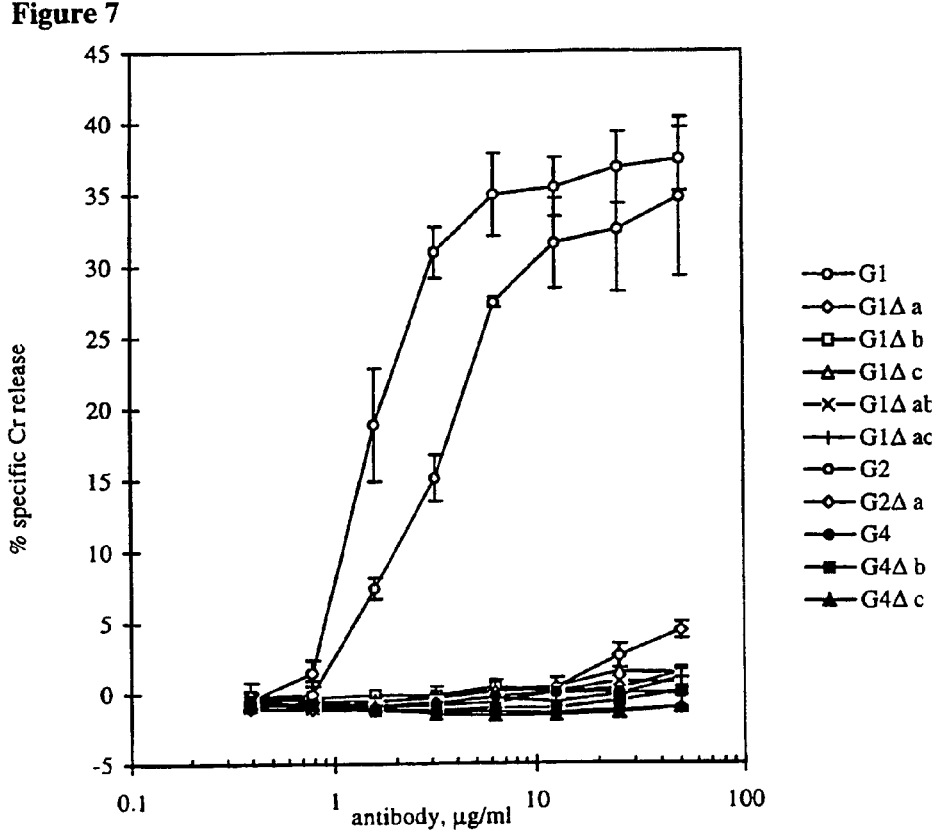

FIG. 7 Complement lysis mediated by CAMPATH-1 series of antibodies. Human PBMC were labelled with $^{51}Cr$ and incubated with the antibodies in the presence of serum as a source of complement. The % specific Cr release is plotted as a measure of lysis occurring.

Figure 8:
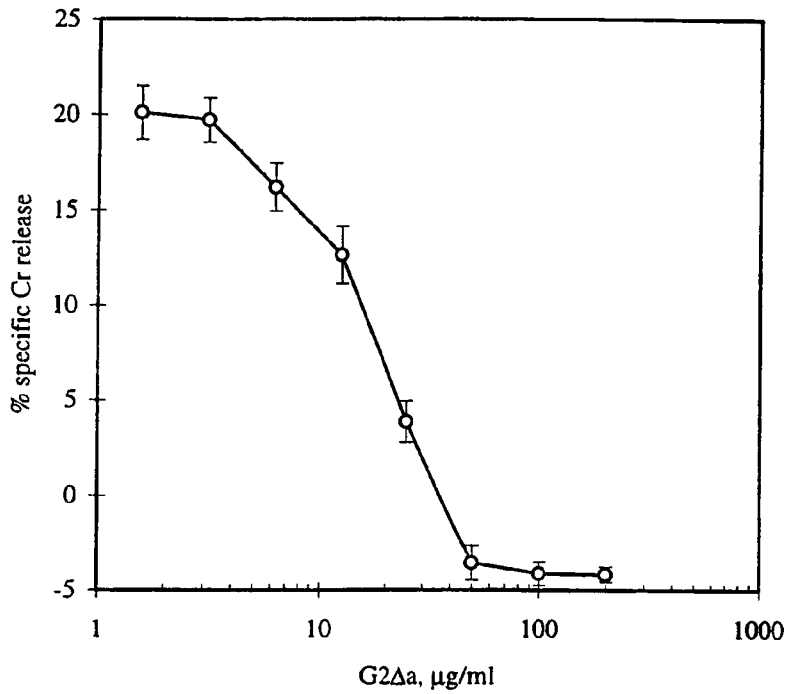

FIG. 8 Inhibition by CAMPATH-1 G2Δa of complement lysis mediated by CAMPATH-1 G1. Complement lysis was carried out as in FIG. 7 but the samples contained a constant amount (6.25 μg/ml final concentration) of CAMPATH-1 G1 and increasing quantities of CAMPATH-1 G2Δa.

Figure 9:
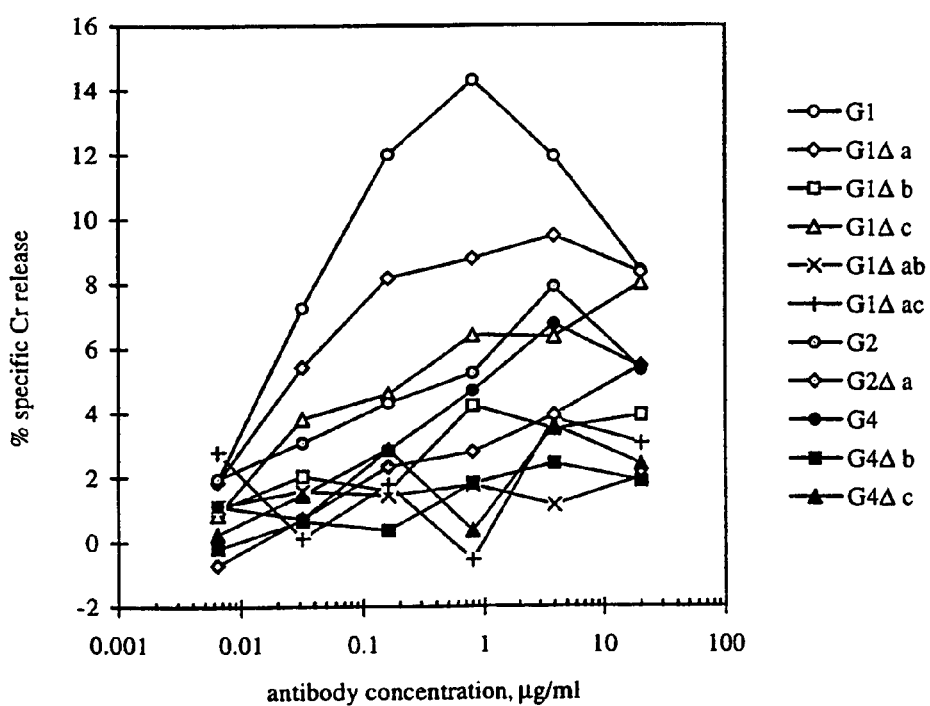

FIG. 9 ADCC mediated by CAMPATH-1 series of antibodies. Human PBMC were labelled with $^{51}Cr$ and incubated with antibody. After washing, the cells were incubated with further PBMC, acting as effector cells, in an effector:target ratio of 20:1. The % specific Cr release is plotted as a measure of lysis occurring.

Figure 10A:
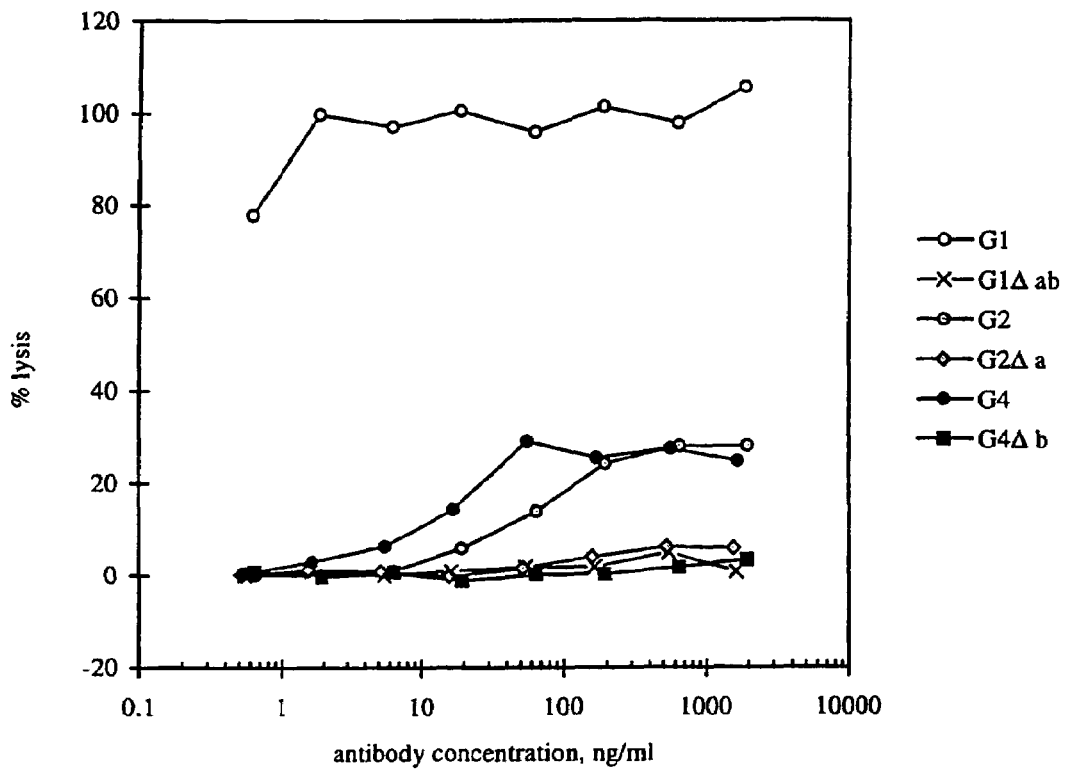

FIG. 10a ADCC of RhD⁺ RBC mediated by Fog-1 series of antibodies

Figure 10B:
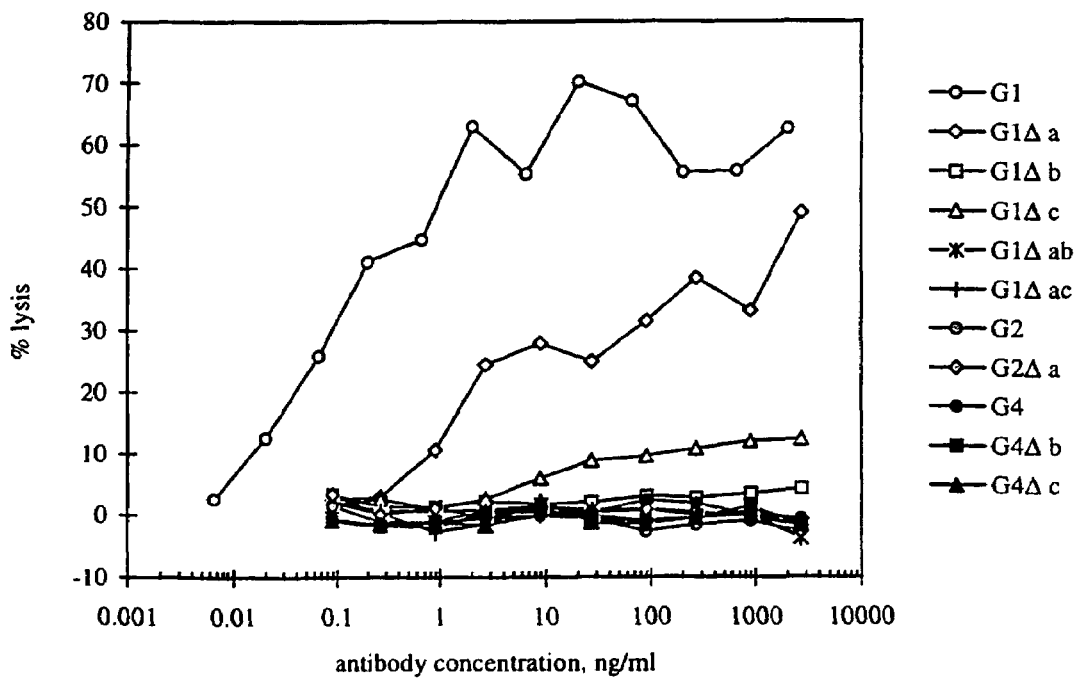

FIG. 10b ADCC of RhD⁺ RBC mediated by Fog-1 series of antibodies

Figure 11A:
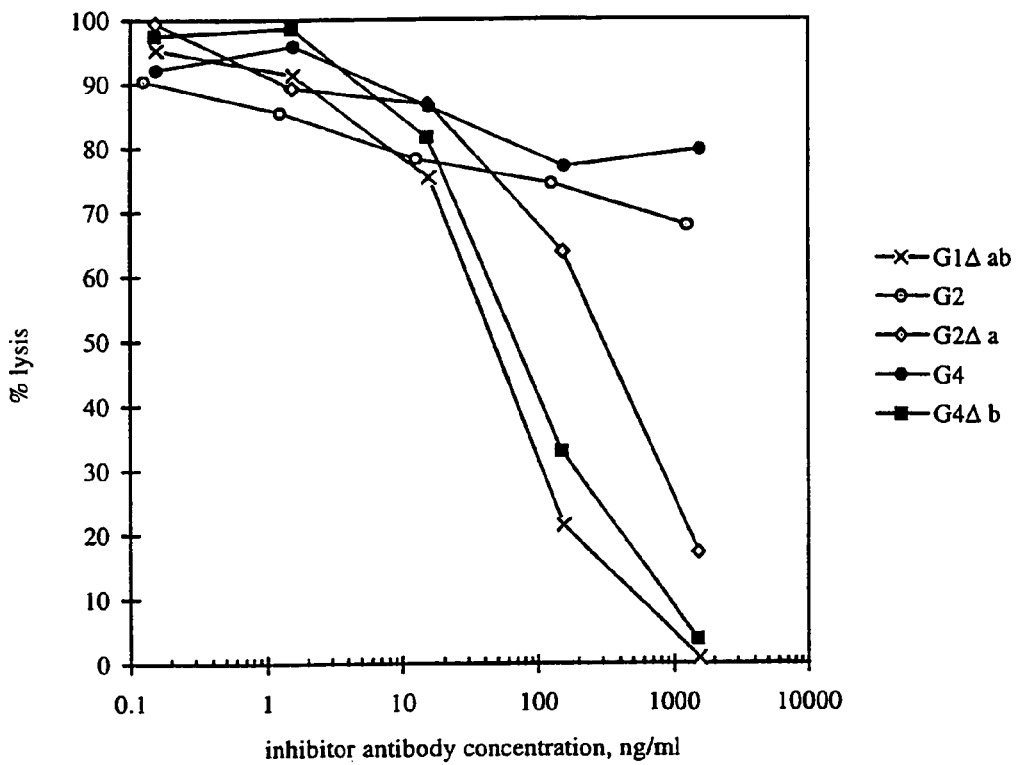
Figure 11B:
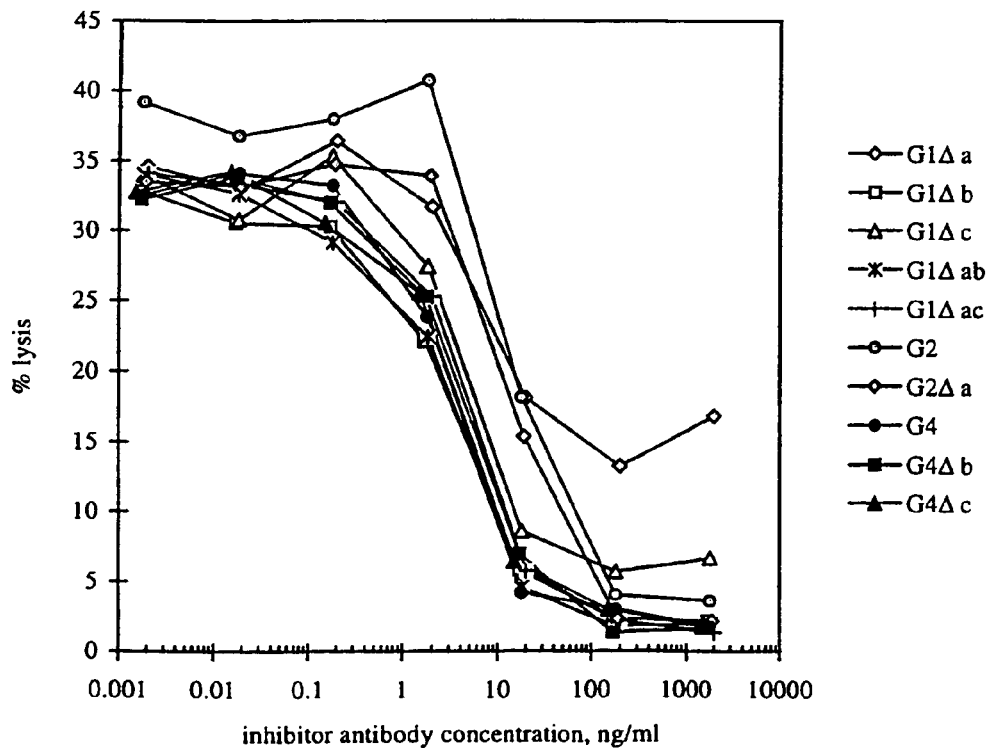

FIG. 11a Inhibition by Fog-1 antibodies of the ADCC of RhD⁺ RBC mediated by Fog-1 G1 at 2 ng/mg FIG. 11b Inhibition by Fog-1 antibodies of the ADCC of RhD⁺ RBC mediated by Fog-1 G1. RBC were sensitized in a mixture of antibodies consisting of a constant amount of Fog-1 G1 (2 ng/ml) and different concentrations of the inhibitor antibodies.

Figure 12:
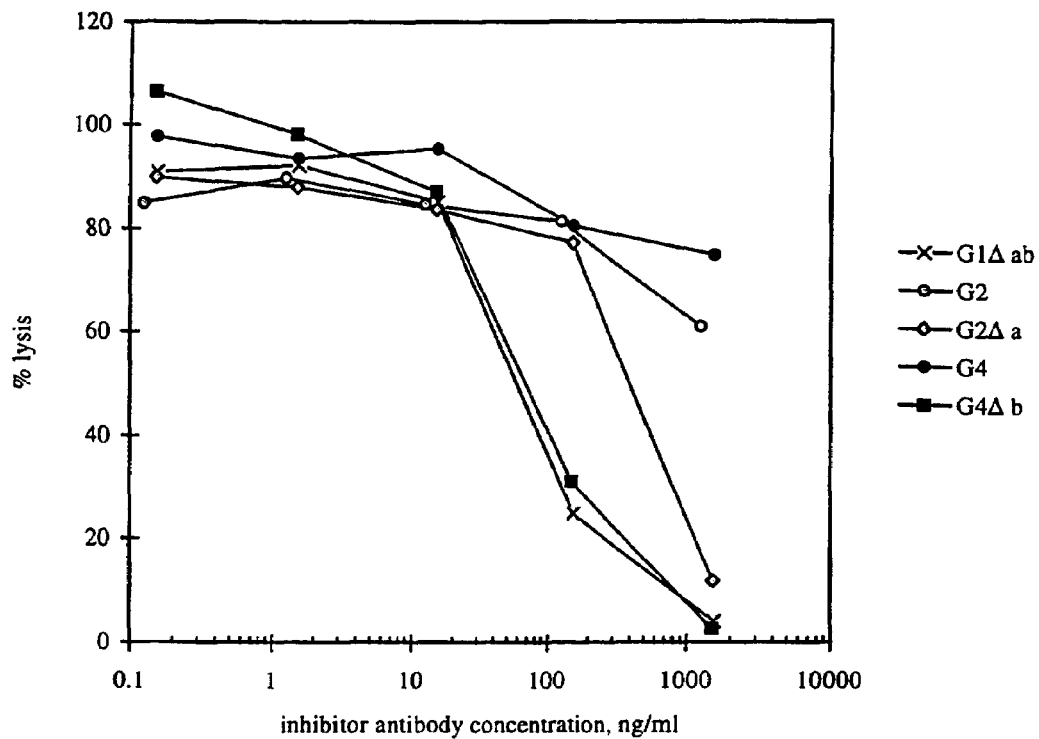
Figure 13Q:
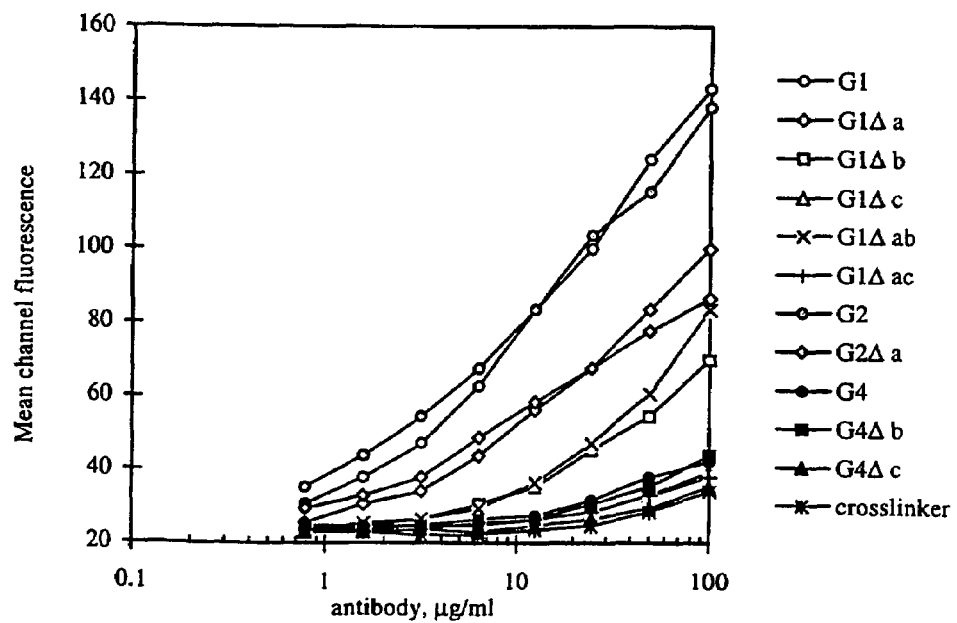

FIG. 12 Inhibition by Fog-1 antibodies of the ADCC of RhD⁺ RBC mediated by polyclonal anti-RhD at 3 ng/mg FIG. 13a Fluorescent staining of FcγRIIa 131H/H-bearing cells. Cells of the transfectant line 3T6+FcγRIIa 131H/H were incubated with the Fog-1 antibodies complexed with goat F(ab')$_2$ anti-human κ and then with FITC-conjugated donkey anti-goat IgG. The fluorescence intensities were measured for 10000 events and the geometric mean channel of fluorescence plotted.

Figure 13B:
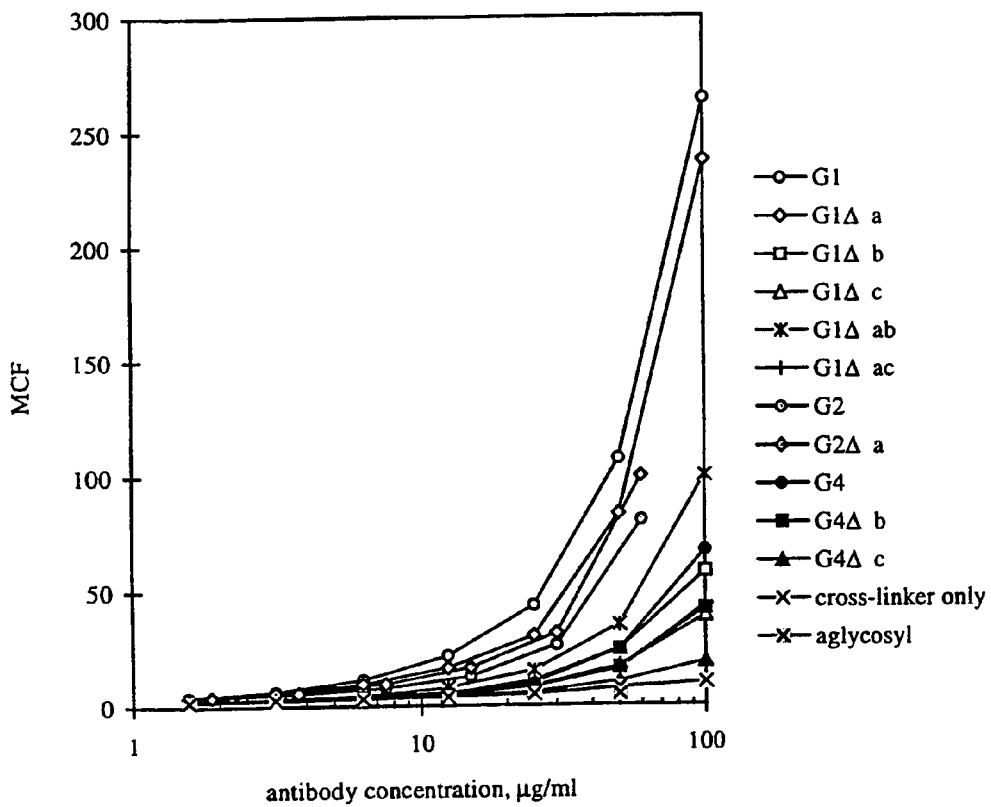

FIG. 13b Fluorescent staining of FcγRIIa 131R/R-bearing cells. Cells of the transfectant line 3T6+FcγRIIa 131R/R were incubated with the Fog-1 antibodies complexed with FITC-conjugated goat F(ab')$_2$ anti-human κ. The fluorescence intensities were measured for 10000 events and the geometric mean channel of fluorescence plotted.

Figure 14Q:
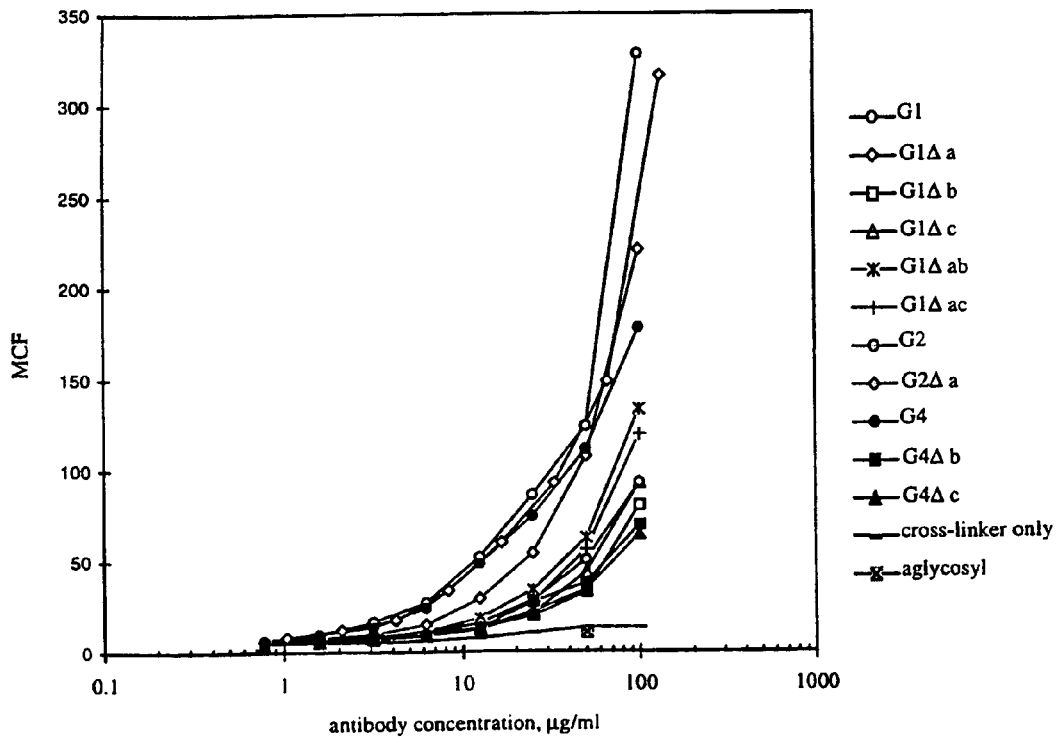

FIG. 14a Fluorescent staining of FcγRIIb1*-bearing cells. The experiment was carried out as in FIG. 13b using the transfectant line 3T6+FcγRIIb1* and complexing the Fog-1 antibodies using a mixture of FITC-conjugated and unlabelled goat F(ab')$_2$ anti-human κ.

FIG. 14b Fluorescent staining of FcγRIIIb NA1-bearing cells. The experiment was carried out as in FIG. 13 using the transfectant line CHO+FcγRIIIb NA1.

Figures 14C, 15:
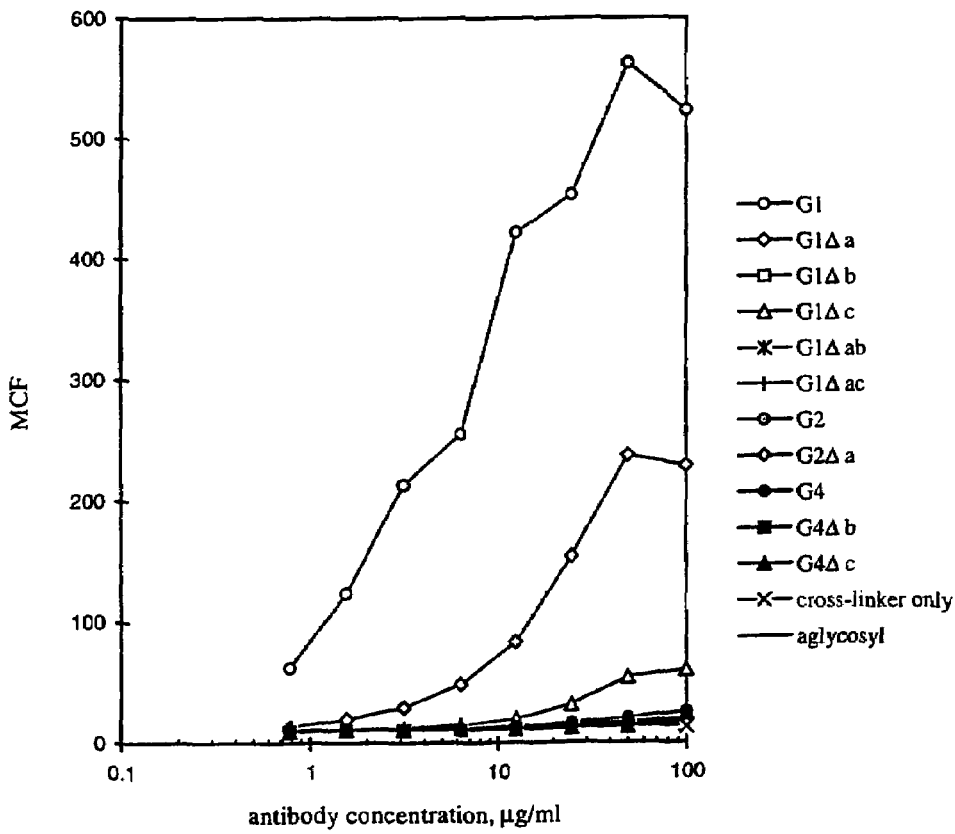

FIG. 14c Fluorescent staining of FcγRIIIb NA2-bearing cells. The experiment was carried out as in FIG. 13 using the transfectant line CHO+FcγRIIIb NA2.

FIG. 15 This shows Table 1, which compares the mutations made to wildtype G1, G2 and G4 sequences.

FIG. 16 This shows Table 2, which is a summary of antibody activities.

FIG. 17 This shows the Sequences of certain modified and wild-type CH2 sequences (G1 (SEQ ID NO:4), G2 (SEQ ID NO:5), G3 (SEQ ID NO:6), G4 (SEQ ID NO:7), G4Δb (SEQ ID NO:11), G4Δc (SEQ ID NO:12), DS111/41 (D2) (SEQ ID NO:8), HuG2/G4 (D10) (SEQ ID NO:11), G1Δab (SEQ ID NO:1), G2Δa (SEQ ID NO:2), and G1Δac (SEQ ID NO:3)).

EXAMPLES

General Materials and Methods

Construction of Expression Vectors

The starting point for the IgG1 constant region was the human IgG1 constant region gene of allotype G1m(1,17) in a version of the vector M13tg131 which contains a modified polylinker (Clark, M. R.: WO 92/16562). The 2.3 kb IgG1 insert thus has a BamHI site at the 5' end and contains a HindIII site adjacent to the BamHI site. At the 3' end, downstream of the polyadenylation signal, the following sites occur in the order 5' to 3': SphI, NotI, BglII, BamHI. The human IgG2 constant region gene had been obtained as a HindIII-SphI fragment in M13tg131 and the HindIII site had been destroyed by digesting with HindIII, filling in the overhanging ends and ligating the ends together again. The SalI-SphI fragment of this vector was cloned to replace the equivalent fragment in the IgG1 vector described above. The human IgG4 constant region gene had been obtained as a HindIII-SmaI fragment in M13tg131 and the HindIII site destroyed. The SmaI site occurs between the 3' end of the CH3 exon and the polyadenylation site so the polyadenylation site was restored by adding the SmaI fragment from the IgG1 vector, which comprises DNA from between the equivalent SmaI site in the IgG1 gene and the SmaI site downstream of the gene in the polylinker.

The first procedure was to introduce an XbaI restriction site between the CH1 and hinge exons, a XhoI site between the hinge and CH2 exons and a KpnI site between the CH2 and CH3 exons in order to facilitate exchange of mutant exon sequences. This was similar to the manipulation of IgG1 and IgG4 genes carried out previously (Greenwood, J., Clark, M. and Waldmann, H. (1993) Structural motifs involved in human IgG antibody effector functions. Eur. J. Immunol. 23, 1098-1104)

To provide the template DNAs, E. coli RZ1032 was infected with the M13 described above and ssDNA prepared. The strain is dut⁻ung⁻ so the ssDNA produced should contain some uridine in place of thymidine.

The oligonucleotides used to introduce the mutations were:

between the hinge and CH2 exons

MO10 5' GGA TGC AGG CTA CTCGAG GGC ACC TG 3'. (SEQ ID NO:13)

between the CH2 and CH3 exons

MO11 5' TGT CCA TGT GGC CCT GGTACC CCA CGG GT 3'. (SEQ ID NO:14)

between the CH1 and hinge exons

MO12 5' GAG CCT GCT TCC TCTAGA CAC CCT CCC T 3' (SEQ ID NO:15)

Restriction sites are underlined.

The oligonucleotides were phosphorylated in 50 μl reactions containing 25 pmol oligonucleotide and 5 u T4 polynucleotide kinase (nbl) in 70 mM Tris HCl pH7.6, 10 mM MgCl$_2$, 100 mM KCl, 5 mM DTT, 0.5 mg/ml BSA, 1 mM ATP. Reactions were incubated at 37 C for 1 h and heated at 70 C for 5 min.

To anneal the mutagenic oligonucleotides to the template DNA, 500 ng uridine-containing DNA and 1 pmol each phosphorylated oligonucleotide were incubated in 20 μl of 40 mM Tris HCl pH7.5, 20 mM MgCl$_2$, 50 mM NaCl at 80 C for 5 min and allowed to cool slowly to 37 C. The volume was increased to 30 μl with the same buffer and DTT added to 7 mM, ATP to 1 mM and dATP, dCTP, dGTP and dTTP each to 250 μM. 5 u T7 DNA polymerase (unmodified, United States Biochemical) and 0.5 u T4 DNA ligase (Gibco BRL) were added and the reaction incubated at room temperature for 16 h to synthesise the mutant strand. The DNA was ethanol precipitated, dissolved 50 μl of 20 mM Tris HCl pH8.0, 1 mM EDTA, 1 mM DTT, 0.1 mg/ml BSA and 1 u uracil DNA glycosylase (New England Biolabs) added. After incubating at 37 C for 2 h, 50 μl 400 mM NaOH was added and the reaction left at room temperature for 5 min to fragment the template strand of DNA. The DNA was ethanol precipitated, dissolved in H$_2$O and transformed into E. coli TG1. Replicative form (RF) DNA was made for a selection of the resultant M13 clones and digested to find clones which contained the required XbaI, XhoI and KpnI restriction sites. Suitable clones were obtained for the IgG1 and 4 vectors but MO12 appeared to be misannealing in the IgG2 vector so the mutagenesis was repeated for IgG2 without this oligonucleotide as the site between the CH1 and hinge exons was not necessary for these experiments. For each vector, the DNA sequences of the exons were confirmed by sequencing.

The changes in CH2 at amino acid positions 327, 330 and 331 (Δa mutation) were to be introduced using the oligonucleotides:

MO22BACK (coding strand):

5' TCT CCA ACA AAG GCC TCC CGT CCT CCA TCG AGA AAA 3' (SEQ ID NO:16)

MO22 (complementary strand):

5' TTT TCT CGA TGG AGG ACG GGA GGC CTT TGT TGG AGA 3' (SEQ ID NO:17)

The changes in CH2 at positions 233 to 236 (Δb and Δc mutation) were to be introduced using the oligonucleotides:

MO7BACK (coding strand and encoding Δc mutation):

5' TCC TCA GCA CCT CCA GTC GCG GGG GGA CCG TCA GTC 3' (SEQ ID NO:18)

MO21 (complementary strand and encoding Δb mutation):

5' GAC TGA CGG TCC CGC GAC TGG AGG TGC TGA GGA 3'. (SEQ ID NO:19)

The mutations were to be introduced by overlap extension PCR which also required the oligonucleotides MO11 and MO10BACK:

5' CAG GTG CC<u>CTCGAG</u>T AGC CTG CAT CC 3' (SEQ ID NO:20)

XhoI restriction site is underlined.

For the Δa mutation, the first set of PCRs used IgG1 and IgG2 templates amplified with MO22 and MO10BACK and with MO22BACK and MO11. For the Δb and Δc mutations, the first set of PCRs used IgG1 and IgG4 templates with MO21 and MO10BACK and with MO7BACK and MO11. In the final product, DNAs originating from a strand primed with MO21 would have the Δb mutation and those originating from MO22BACK would carry the Δc mutation. Each PCR contained about 30 ng M13tg131+constant region ssDNA, 25 pmol each oligonucleotide and 1 u Pwo DNA polymerase (Boehringer Mannheim) in 50 ul of 10 mM Tris HCl, pH8.85, 25 mM KCl, 5 mM $(NH_4)_2SO_4$, 2 mM $MgSO_4$ and 250 μM each dATG, dCTP, dGTP and dTTP. The reactions were subjected to 14 cycles of 94 C, 30 s; 50 C, 30 s; 72 C, 60 s, followed by 72 C, 5 min to end. Bands representing product DNAs of the expected sizes were excised from low melting point agarose and melted in 100 μl $H_2O$. For each mutation, the two initial PCR products were joined together by overlap extension PCR. About 4 μl total of the melted gel slices, such that the initial PCR products were in equimolar amounts, were mixed with 25 pmol each MO10BACK and MO11 and other components as above. The PCR was carried out over 18 cycles as above except that the annealing temperature was reduced from 50 C to 48 C. The products obtained, which contained the entire CH2 exon, were purified and digested with XhoI and KpnI. The RF DNAs of the mutated M13tg131+constant region vectors, containing the extra restriction sites as described above, were digested with XhoI and KpnI to remove the existing CH2 DNAs and the mutant CH2 regions ligated in. The DNA samples were transformed into *E. coli* TG1. DNA of representative clones was sequenced to identify correctly mutated constant regions.

In order to obtain IgG1 vectors with both Δa and Δb or Δc, DNA, representing a Δa mutant, was used as the template for a second round of PCRs to introduce the Δb and Δc mutations as described above.

The IgG1, 2 and 4 wild type and mutated constant region genes were each excised from RF DNA as a BamHI-NotI fragment and cloned into the modified CAMPATH Hu4VH HuIgG1 pSVgpt vector (Clark, M. R.: Lynxvale Binding Molecules as above) to replace the existing constant region. The resulting vectors were designated pSVgptCAMPATHHu4VHHuIgG1Δa, etc. The vector also contains the gpt gene to allow selection in mammalian cells, the murine immunoglobulin heavy chain enhancer and the CAMPATH-1 Hu4VH variable region DNA so that it carries a complete heavy chain gene which can be expressed in mammalian cells. The CAMPATH-1 humanised light chain gene exists in the expression vector CAMPATH HuVL pSVneo (Reichmann, L., Clark, M. R., Waldmann, H. and Winter, G. (1988) Nature 332, 323-327).

The Fog1 variable region DNAs (Bye, J. M., Carter, C., Cui, Y., Gorick, B. D., Songsivilai, S., Winter, G., Hughes-Jones, N. C. and Marks, J. D. (1992) Germline variable region gene segment derivation of human monoclonal anti-Rh(D) antibodies. J. Clin. Invest. 90, 2481-2490) were obtained in the vector pHEN1. They were amplified by PCR, using the oligonucleotides:

FOG1VHBACK 5' TCC ACA GGT GTC CAC TCC CAG GTG CAT CTA CAG CAG 3' (SEQ ID NO:21)

FOG1VHFOR 5' GAG GTT GTA AGG ACT CAC CTG AGG AGA CGG TGA CCG T 3' (SEQ ID NO:22)

FOG1VKBACK 5' TCC ACA GGT GTC CAC TCC GAC ATC CAG ATG ACC CAG 3' (SEQ ID NO:23)

FOG1VKFOR 5' GAG GTT GTA AGG ACT CAC GTT TGA TCT CCA GCT TGG T 3' (SEQ ID NO:24)

The 5' portion of the insert in the vector M13VHPCR1 (Orlandi, R., Gussow, D. H., Jones, P. T. and Winter, G. (1989) Proc. Natl. Acad. Sci. USA 86, 3833), comprising the promoter and DNA encoding the signal peptide was amplified using the universal M13 reverse primer and VO3:

5' GGA GTC GAC ACC TGT GGA GA 3' (SEQ ID NO:25)

DNA, 3' of the $V_H$ in M13VHPCR1 and representing the 5' end of the $V_H$-$C_H$ intron, was obtained by PCR using the universal M13-40 primer and VO4:

5' GTG AGT CCT TAC AAC CTC TC 3' (SEQ ID NO:26)

These two segments of DNA were joined sequentially to both the FOG-1 $V_H$ and FOG-1 $V_K$ amplified DNA by overlap extension PCR as described above. The BamHI restriction site internal to the FOG-1 $V_H$ was deleted by the same method using oligonucleotides which removed the recognition site without changing the amino acids encoded. The compete PCR products were cloned into M13mp19 as HindII-BamHI fragments and their DNA sequences confirmed.

The HindIII-BamHI fragment containing the Fog-1 $V_H$ was used to replace the fragment containing the CAMPATH-1 $V_H$ in the pSVgpt vectors described above, giving expression vectors designated pSVgptFog1VHHuIgG2, etc. For the IgG1 vectors, the extra HindIII restriction site at the 5' end of the constant region DNAs meant that it was not possible to simply exchange the HindIII-BamHI variable region fragment. Instead, the relevant pSVgptCAMPATHHu4VHHuIgG1 vectors were digested with HindIII. Linkers, designed to delete the HindIII site and add a BamHI site, were ligated onto the cut ends. The DNAs were then digested with BamHI and NotI so that the constant regions could be isolated and these were cloned into pSVgptFog1VHHuIgG2 to replace the IgG2 constant region.

The HindIII-BamHI fragment containing the Fog-1 $V_K$ was transferred to the vector pSVhyg-HuCK (Orlandi et al., 1989)

which already contains the murine immunoglobulin heavy chain enhancer and the human κ constant region gene. The resulting expression vector was called pSVhygFog1VKHuCK.

Production of Antibodies

10 μg of each heavy chain expression vector and 20 μg of the relevant light chain expression vector were linearised by digestion with PvuI and combined in 50 μl of $H_2O$. Cells of the non-secreting rat myeloma line, YB2/0, were grown to semi-confluency in Iscove's modified Dulbecco's medium (IMDM) with 5% foetal bovine serum (FBS). $10^7$ cells were collected by centrifugation, resuspended in 0.5 ml medium and transferred to a GenePulser cuvette (BioRad). The DNA was added and the mixture incubated on ice for 5 min. The cells were given one pulse of 960 μF/170 V and returned to ice for 15 min before being placed in a flask in 20 ml IMDM+ 10% FBS. They were incubated at 37 C, 5% $CO_2$ in a humidified atmosphere. After 24 h, the volume was doubled and the medium made selective by addition of mycophenolic acid to 0.8 μg/ml and xanthine to 250 μg/ml. The cells were aliquotted over two 96-well plates. About 18 d after selection was applied, colonies were visible and the supernatants were assayed for the presence of IgG by ELISA. Briefly, microtitre-plate wells were coated with goat anti-human IgG, Fc-specific antibodies (Sigma) and then incubated with 5-fold dilutions of the supernatants. Bound antibody was detected by incubating with HRPO-conjugated goat anti-human κ antibodies (Seralab) and developing the assay with o-phenylenediamine substrate. Cells from wells containing the highest amounts of antibody were expanded and stocks cryopreserved.

The cell line secreting the highest amounts of Ab was expanded to 500 ml in IMDM+2% FBS to provide saturated supernatant for antibody purification. The supernatant was cleared by centrifugation and made 0.1 M Tris HCl pH8.0. Protein A-agarose (Sigma) was added and the mixture stirred at 4 C for 16 h. The agarose beads were collected into a column and washed with 0.1 M Tris HCl pH8.0, followed by 10 mM Tris HCl pH8.0. The antibody was eluted with 1 ml aliquots of 0.1 M glycine pH3.0 into 100 μl samples of 1 M Tris HCl pH8.0 and the fractions containing significant amounts of protein were identified from $A_{280nm}$ readings. These fractions were dialysed against PBS, filter-sterilised and the $A_{280nm}$ remeasured to give the approximate antibody concentration (concentration=$A_{280nm}$×0.714 mg/ml).

The purity and integrity of the antibodies were established by reducing SDS-PAGE, using 12.5% acrylamide. The concentrations were checked in an ELISA which used goat anti-human κ antibodies (Seralab) as the capture reagent and biotinylated goat anti-human κ antibodies (Sigma) followed by ExtrAvidin-HRPO (Sigma) for detection. This meant that the nature of the heavy chain was unlikely to influence the level of binding obtained.

Rosetting of FcγRI Transfectants

Washed $R_2R_2$ RBC were incubated with Ab samples in 100 ml PBS in 96-well plates at room temperature for 1 h. The RBC were washed three times, resuspended in PBS and incubated at 37 C for 40 min with transfectants expressing FcγRI cDNA, B2KA (S. Gorman and G. Hale, unpublished), growing in 96-well plates. The supernatant was discarded and the wells washed once to remove excess RBC. For each well, 200 B2KA cells were examined and the number with RBC rosettes noted. The mean percentage and standard deviation for triplicate wells was plotted. Alternatively, the sensitized RBC and B2KA cells were mixed in microcentrifuge tubes, pelleted and gently resuspended before transfer to a microscope slide.

Fluorescent Staining of FcγR Transfectants

Transfectants expressing FcγRI cDNA, B2KA and 3T3+ FcγRIa+γ-chain (van Urgt, M. J., Heijnen, I. A. F. M., Capel, P. J. A., Park, S. Y., Ra, C., Saito, T., Verbeek, J. S. and van de Winkel, J. G. J. (1996) FcR γ-chain is essential for both surface expression and function of human FcγRI (CD64) in vivo. Blood 87, 3593-3599), were obtained as single cell suspensions in phosphate-buffered saline containing 0.1% (w/v) $NaN_3$, 0.1% (w/v) BSA (wash buffer) following treatment with cell dissociation buffer (Gibco BRL). Cells were pelleted at $10^5$ cells/well in 96-well plates, resuspended in 100 μl dilutions of the CAMPATH-1 or Fog-1 Ab and incubated on ice for 30 min. Cells were washed three times 150 μl/well wash buffer and similarly incubated with 20 μg/ml biotin-conjugated goat anti-human κ-chain Ab (Sigma) and then with 20 μg/ml ExtrAvidin-FITC (Sigma). After the final wash, cells were fixed in 100 μl wash buffer containing 1% (v/v) formaldehyde. Surface expression of FcγRI was confirmed by staining with CD64 mAb (Serotec) and FITC-conjugated goat and mouse IgG Ab (Sigma). Fluorescence intensities were measured on a FACScan (Becton Dickinson).

For transfectants bearing FcγRII, 3T6+FcγRIIa 131H/H, 3T6+FcγRIIa 131R/R (Warmerdam, P. A. M., van de Winkel, J. G. J., Gosselin, E. J., and Capel, P. J. A. (1990) Molecular basis for a polymorphism of human Fcγ receptor II (CD32). J. Exp. Med. 172, 19-25; Warmerdam, P. A. M., van de Winkel, J. G. J., Vlug, A., Westerdaal, N. A. C. and Capel, P. J. A. (1991) A single amino acid in the second Ig-like domain of the human Fcγ receptor II is critical for human IgG2 binding. J. Immunol. 147, 1338-1343) and 3T6+FcγRIIb1* (Warmerdam, P. A. M., van den Herik-Oudijk, I. E., Parren, P. W. H. I., Westerdaal, N. A. C., van de Winkel, J. G. J. and Capel, P. J. A. (1993) Int. Immunol. 5, 239-247) the antibodies were complexed before being incubated with the cells. For FcγRIIa 131H/H, the antibodies were mixed with equimolar amounts of goat F(ab')$_2$ anti-human κ (Seralab) and incubated at 37 C for 1 h. The complexes were then mixed with the cells and the assay continued as above except that the detecting antibody was FITC-conjugated donkey anti-goat IgG (Serotec). For FcγRIIa 131R/R, the complexes were made using equimolar amounts of FITC-conjugated goat F(ab')$_2$ anti-human κ (Seralab), and for FcγRIIb1*, the complexes were made using equimolar amounts of a 1:1 mixture of FITC-conjugated and unlabelled goat F(ab')$_2$ anti-human κ. Thus for these receptors only one incubation step was needed.

For transfectants bearing FcγRIIIb, CHO+FcγRIIIb NA1 or NA2 (Bux, J., Kissel, K., Hofmann, C. and Santoso, S. (1999) The use of allele-specific recombinant Fc gamma receptor IIIb antigens for the detection of granulocyte antibodies. Blood 93, 357-362), staining was carried out as described for 3T6+FcγRIIa 131H/H cells above.

Red Cell Sensitization

Group O $R_1R_1$ RBC were washed in PBS and resuspended in RPMI+10% FBS at a final concentration of 5% v/v. 10 μl of cells was added to 50 μl mAb or RPMI/FBS in V-bottom well plates and incubated for 60 min at 37 C. In some experiments, the mAb were serially diluted in RPMI/FBS to achieve a range of red cell-bound IgG. In competition experiments, the red cells were sensitized in a mixture of 25 μl competing mAb and 25 μl of wild-type mAb or 25 μl serum containing alloantibodies. After sensitization, cells were washed 4 times with 200 μl volumes of PBS and resuspended in 50 μl RPMI/FBS (final concentration=1% v/v). In all experiments, an aliquot of cells (E-IgG) was used in the chemiluminescence (CL) assay and an aliquot was assayed by flow cytometry to determine the level of red cell-bound IgG.

Chemiluminescence Assay

PBMC were isolated by density gradient centrifugation from EDTA-anticoagulated blood pooled from 6 normal donors. PBMC were washed 4 times with PBS containing 1% globulin-free BSA and then resuspended at $2 \times 10^6$/ml in Hank's Balanced Salt Solution (HBSS) containing 25% RPMI and 2.5% FBS. Aliquots (100 µl) were dispensed into 96 flat-bottomed white opaque plates and incubated for 2 h at 37 C in a humidified atmosphere of 5% $CO_2$ in air. The plates were then placed in a luminometer (Anthos Lucy 1, Labtech International, Uckfield, UK) and 100 µl HBSS containing $4 \times 10^{-4}$ M luminol (Sigma) and 20 µL E-IgG were added to each well. The CL response was then monitored at 37 C for 60 minutes.

Determination of Red Cell Bound IgG

25 µl aliquots of E-IgG were transferred to a V-bottom well plate, washed once with PBS, centrifuged to a pellet and resuspended in 50 µl F(ab)$_2$ FITC-anti-IgG (diluted ⅟₃₀ in PBS/1% BSA). After 30 min at room temperature, the cells were washed once with 200 µl PBS/BSA and kept on ice until analysed by flow cytometry (EPICS XL-MCL, Coulter Electronics, Luton, UK). The mean channel fluorescence was recorded.

Mean channel fluorescence was converted to IgG molecules/cell by use of a standard curve which was prepared by adding 100 µl of 5% v/v $R_1R_1$ cells to 900 µl of serial 2 fold dilutions of human monoclonal IgG1 anti-D (BRAD-5). Sensitized red cells were washed 3 times with PBS/BSA and resuspended to 1% v/v in PBS/BSA. 25 µl aliquots were removed and analysed by flow cytometry as described above. The remaining red cells were counted, centrifuged to a pellet, lysed in a buffer containing Triton X-100 and IgG in lysates was determined by ELISA as described by Kumpel (Kumpel, B. M. (1990). A simple non-isotopic method for the quantitation of red cell-bound immunoglobulin. *Vox Sanguinis*, 59, 34-39). The number of IgG molecules bound per red cell was deduced from the IgG concentration and the number of red cells from which each lysate was prepared. A standard curve was then plotted comparing fluorescence intensity with the number of IgG molecules bound per red cell.

Complement Lysis Mediated by CAMPATH-1 Series of Antibodies 100 ml venous blood from a healthy volunteer was defibrinated and components separated by density gradient centrifugation using Ficoll-Paque Plus (Pharmacia). The serum and mononuclear cell layers were removed to fresh tubes. The cells were diluted into Iscove's modified Dulbecco's medium (IMDM) and collected by centrifugation. The cells were washed twice in IMDM whilst being combined into one pellet which was resuspended in 200 µl IMDM. 900 µCi sodium [$^{51}$Cr] chromate was added and the cells incubated at 37 C for 40 min. 10 ml IMDM was added and the cells pelleted. The cells were washed twice and resuspended in IMDM at approximately $6 \times 10^6$ cells/ml. 50 µl aliquots of labelled cells were added to antibody samples in 50 µl IMDM in 96-well plate wells. 100 µl retained serum diluted 1:1 with IMDM was added to each well and the plates incubated at 37 C for 1 h. The plates were centrifuged and the supernatants were sampled and the relative amounts of $^{51}$Cr released were measured in a γ-counter. The level of spontaneous release was obtained from samples were no antibody was added and a measure of the total amount of $^{51}$Cr available for release was found from similar samples taken after resuspending the cells. The % specific $^{51}$Cr release was calculated from the formula:

$$(\text{sample counts} - \text{spontaneous counts}) \times 100 / (\text{total counts} - \text{spontaneous counts})$$

The means and standard deviations of the triplicate samples were plotted.

For the inhibition of complement lysis, antibody samples contained a constant amount (6.25 µg/ml final concentration) of CAMPATH-1 G1 and increasing quantities of CAMPATH-1 G2Δa.

ADCC Mediated by CAMPATH-1 Series of Antibodies

Peripheral blood mononuclear cells were prepared as described above. After washing, the cells were resuspended in IMDM supplemented with 5% FBS and transferred to flask which had been coated with CD3 antibody. The cells were grown at 37 C, 5% $CO_2$ for three days. 5% of the cells were labelled with $^{51}$Cr for use as target cells, washed and resuspended at $6 \times 10^5$ cells/ml in IMDM+5% FBS. 50 µl aliquots were added to wells of 96-well plates containing 50 µl samples of antibodies in IMDM+5% FBS. The target cells and antibodies were incubated at 37 C for 1 h, RBC added as carriers and the cells pelleted. The cells were washed twice in IMDM. The remaining mononuclear cells were collected by centrifugation and resuspended at $4 \times 10^6$ cells/ml in IMDM+5% FBS and 150 µl added to each well resuspending the target cells in the process. This gives an effector:target ratio of 20:1. The cells were centrifuged gently and placed in a tissue culture incubator for 6 h. Supernatant was sampled and specific $^{51}$Cr release determined as described above. The mean values of specific release for the duplicate samples was plotted against the final antibody concentrations.

EXAMPLE 1

Generation and Basic Characterisation of Antibodies

The mutations chosen to eliminate the effector functions are shown in Table 1 (FIG. 15). The Δa mutation made in IgG1 and IgG2 genes introduces the IgG4 residues at positions 327, 330 and 331. Similarly, the IgG2 residues at positions 233-236 were introduced into IgG1 and IgG4 but, since IgG2 has a deletion at 236 where the other subclasses have a glycine residue, the mutation was made omitting (Δb) or including (Δc) G236.

Vectors allowing expression of CAMPATH-1 or Fog-1 $V_H$ DNA in conjunction with the wildtype or mutant constant region genes were cotransfected with the appropriate light chain expression vectors into rat myeloma cells. Stable transfectants were isolated, expanded and Ab purified from the supernatant on protein A-agarose.

CAMPATH-1H was selected as it provides a good targeting system for studying complement and cell mediated lysis in vitro.

For the Fog-1 Ab, a precipitate formed after purification but, once this had been removed by filter-sterilisation, no further precipitation was noticed. Ab concentrations were estimated from the absorbance at 280 nm and were adjusted where necessary following an ELISA which measures the relative amounts of κ-chain present. The Ab were subjected to reducing SDS-PAGE. Each sample showed two bands with apparent molecular weights of approximately 25 and 55 kDa which represent the expected sizes of the light and heavy chains. There was no discernible difference in size between the heavy chains of each Ab series but both chains of the Fog-1 Ab appeared to be slightly smaller than their CAM- PATH-1 counterparts. The fact that the heavy chain within each series appeared to have the same apparent molecular weight indicates that the mutations did not cause any extensive differences in the glycosylation of the proteins. For the Ab with CAMPATH-1 specificity, the yield after purification varied from 0.6 to 9 µg/ml supernatant whereas the yield of soluble Fog-1 Ab was between 3 and 20 µg/ml. There was no correlation in the ranking of the purification yields for the two series of antibodies suggesting that none of the mutations affected the production of the Ab or their ability to bind protein A.

The specificities of the two series of Ab were then tested. The CAMPATH-1 Ab were shown to compete with clinical grade CAMPATH-1H in the binding of the anti-CAMPATH-1 idiotype mAb, YID13.9. The Fog-1 Ab where able to agglutinate RhD$^+$ RBC in the presence of anti-human IgG Ab as cross-linking reagents. Similarly, the IgG subclasses of the Fog1 Ab were examined by coating RhD$^+$ RBC with the different Ab and looking at the agglutination pattern using anti-Glm(a), anti-IgG2 or anti-IgG4 Ab as the cross-linking Ab. The result indicated that the antibodies were of the correct subclasses. The agglutination of RhD$^+$ RBC by Fog-1 IgG1 and anti-Glm(a), by Fog-1 IgG2 and anti-IgG2 and by Fog-1 IgG4 and anti-IgG4 was then carried out in the presence of excess Ab from the CAMPATH-1 series. The CAMPATH-1 Ab were able to inhibit the agglutination, by competing for the cross-linking reagent, only where they were of the same subclass as the Fog-1 Ab, thus verifying their subclasses.

EXAMPLE 2

FcγRI Binding

RBC with approximately 30 000 RhD sites per cell ($R_2R_2$) were coated with each of the 11 Fog-1 Ab over a range of concentrations and added to human FcγRI-expressing transfectants, B2KA, growing in wells. After incubation, excess RBC were washed away and the percentage of B2KA cells rosetted by RBC was recorded (FIG. 1). For G1 and G1Δa, where IgG4 residues are included at positions 327, 330 and 331, similar levels of resetting were achieved, with half-maximal resetting occurring when the RBC were coated with Ab at about 0.1 µg/ml, a concentration at which Fog-1 Ab would be expected to occupy approximately one-third of the RhD sites. Slightly higher concentrations of G4 were needed to obtain the same levels of resetting. No rosettes were formed when using RBC coated with the G1 and G4 Ab containing the Δb and Δc mutations or the G2 Ab. In the experiment shown in FIG. 1, the highest coating concentration tested was 10 mg/ml, predicted to correspond to approximately 90% occupancy of RhD sites. The experiment was repeated using coating concentrations of up to 80 mg/ml, essentially saturating the RhD sites, and still no rosettes were seen for G2 and the Ab containing the Db or Dc mutations and thus incorporating IgG2 residues in the lower hinge region. This indicates that, even when the RBC were coated with these Ab at the maximum density for this antigen, there was insufficient IgG/FcγgRI interaction for rosette formation.

Centrifuging the sensitized RBC and B2KA cells together before observing rosettes on a microscope slide was found to give a higher proportion of rosettes than incubating the cells in wells so this method was used to investigate the inhibition of rosette formation. $R_2R_2$RBC were coated with a mixture of 1 mg/ml Fog-1 G1 and different amounts of Fog-1 G2Da or Fog-1 G4Db before mixing with B2KA cells. When 1 µg/ml Fog-1 G1 was used alone, the coated RBC formed rosettes on 95% of the B2KA cells whereas sensitization in the presence of 64 mg/ml G2Δa or G4Δb completely abolished the resetting (data not shown).

The binding of Ab from both series to two different cell lines, which express the FcγRI cDNA on their surface, was measured by fluorescent staining. FIG. 2 shows representative experiments. The level of surface-expressed FcγRI, as detected using the CD64 Ab, was higher for the 3T3 transfectants than for the B2KA line and this reflects in the higher signals obtained when measuring binding via the Fc. For both series, the G1 and G1Δa Ab bound to the receptor with the same apparent affinity indicating that the mutations at positions 327, 330 and 331 did not significantly affect the interaction. The binding of G4 Ab was approximately three-fold lower than that of the G1 and G1Δa Ab. Little binding was seen for the G2 Ab or any of the other mutant Ab, suggesting that the Δb and Δc mutations in IgG1 and IgG4 were sufficient to reduce binding to FcγRI by at least $10^4$-fold. Ab containing the Δc mutation, especially G1Δc, showed a small degree of binding to FcγRI at the highest concentrations tested if the level of fluorescence is compared to the background or to the equivalent Ab with the Δb mutation. If the fluorescence intensity histograms are overlaid, as seen in FIG. 3 for the highest concentrations of CAMPATH-1 Ab and B2KA cells, the plots for G1 and G1Δa coincide. There is a clear difference between the histograms for the G1Δb and G1Δc Ab.

EXAMPLE 3

FcγRI Triggering Measured By Chemiluminescence

In order to measure functional activity through FcγRI/II, the chemiluminescent (CL) response of monocytes to RBC sensitized with Ab from the Fog-1 series was measured and plotted in relation to the number of Ab molecules bound per RBC (FIG. 4). A difference between the G1 and G1Δa Ab is seen with higher amounts of Ab but both are give higher responses than the G4 Ab across the range of Ab concentrations. Significant triggering is achieved by the G1Δc Ab and, to a lesser extent, by G1Δac and G4Δc but the other Ab do not give any response.

Ab, which were known to be deficient in the triggering of FcγRI from the previous section, were mixed in increasing concentrations with a constant amount of Fog-1 G1 and used to sensitize RBC. The CL response to the RBC is shown in FIG. 5. By comparing the CL response to that obtained when titering G1 alone, it appears that six of the eight Ab inhibit the reaction to an extent which predicted if it is assumed that the mutants displace the active G1 from RBC in proportion to their relative concentrations. For G2, the inhibitory effect is delayed in that about three-fold more G2 is needed to give the same amount of inhibition. G1Δc inhibits to approximately the same extent as the other mutants except that the response is not reduced to zero.

Two papers which have discussed the usefulness of chemiluminescence in predicting the severity of in-vivo pathology are Hadley (1995) Transfusion Medicine Reviews 9:302-313 and Hadley et al (1998) Br J Obstet Gynaecol 105: 231-234.

In these assays a result above 30% chemiluminescence produced by the BRAD-5 monoclonal antibody control would be predictive of in-vivo pathology in HDN. Thus those antibodies which can block to levels below 30% should be suitable for therapy.

One of the mutant Ab, Fog-1 G2Δa was tested for its ability to inhibit the CL response to sera containing clinically significant Ab. The sera contained anti-RhD Ab or antiC+D and, in the absence of inhibitor, gave CL responses of greater than 30% on this scale which is indicative of severe haemolytic disease of the newborn and the need for intrauterine transfusions. The sera were mixed with different concentrations of G2Δa, the mixtures used to sensitise RBC and the responses of monocytes measured (FIG. 6). The addition of G2Δa Ab reduced the CL signals due to all five anti-RhD sera to below the 30% cut-off. The amount of Ab needed to achieve this varied from 16-260 μg/ml, the range presumably reflecting the differing amounts and affinities of anti-RhD Ab in the serum. There are two control sera. The anti-K serum cannot be blocked at all by G2Δa as its reactivity is directed towards a different antigen on the RBC. Only part of the activity of the anti-C+D serum could be inhibited by G2Δa.

EXAMPLE 4

Activity in Complement Lysis

FIG. 7 shows that all the mutations made to the G1 and G2 CAMPATH-1 antibodies dramatically reduced their ability to mediate complement lysis. When the assay was carried out using a constant amount of G1 and different amounts of G2Δa (FIG. 8), the G2Δa antibody was able to block the killing of PBMC by CAMPATH-1 G1.

EXAMPLE 5

Activity in ADCC

The ability to mediate ADCC was measured for the CAMPATH-1 antibodies using human PBMC as target cells (FIG. 9) and for the Fog-1 antibodies using RhD$^+$ RBC as target cells (FIGS. 10 and 10b). FIG. 9 shows mixed abilities of the CAMPATH-1 antibodies in ADCC, with some of the mutants having very low activities. FIGS. 10 and 10b show that the Fog-1 antibody mutants G1Δab, G1Δac, G2Δa, G4Δb and G4Δc were unable to support any killing of the RBC. In FIG. 10, some lysis of RBC sensitized with G2 or G4 is seen but these antibodies have no apparent activity in the assay of FIG. 10b. This demonstrates the observation that the degree of lysis may be dependent on the donor of the effector cells and may even vary when using effector cells taken from the same donor at different times. However, for the mutants listed above, no activity above background levels has been seen although a range of effector cell donors have been tested.

Some of the Fog-1 antibodies were used to try to inhibit the ADCC of RhD$^+$ RBC by Fog-1 G1 (FIGS. 11 and 11b) and by a clinical sample of anti-RhD serum (FIG. 12). The figures show that all of the antibodies tested were able to inhibit ADCC when mixed with the active antibodies prior to RBC sensitisation. The Fog-1 mutant antibodies G1Δb, G1Δab, G1Δac, G4Δb and G4Δc were particularly effective at blocking ADCC.

EXAMPLE 6

FcγRII Binding

FIGS. 13, 13b and 14 show the binding of complexes of antibodies from the Fog-1 series to cells bearing FcγRIIa 131H/H, FcγRIIa 131R/R and FcγRIIb1* respectively. It is necessary to form antibody complexes when measuring binding to these receptors due to their low affinity for individual antibody molecules. FcγRIIa 131H/H is an allotype of FcγRIIa to which IgG2 antibodies are expected to bind strongly and, indeed, G1 and G2 show a strong binding activity (FIG. 13). Addition of the mutations to these two antibodies appears to give a stepwise reduction in the levels of binding and the G1Δc and G1Δac antibodies have only background levels of binding as exhibited by the G4 antibodies. FIG. 13b shows that the antibodies have different relative activities when binding to the 131R allotype of FcγRIIa but the mutations made to the wildtype G1 antibody again decrease binding to the receptor. All of the antibodies show significantly more binding to the inhibitory receptor, FcγRIIb1*, than the negative control samples of cross-linking F(ab')$_2$ alone or an aglycosyl IgG1 antibody complexed with the F(ab')$_2$ (FIG. 14). Although the binding of most mutants is reduced relative to the corresponding wildtype antibodies, some mutants show binding within two-fold of that exhibited by the wildtype G1 antibody.

EXAMPLE 6b

FcgRIII Binding

FIGS. 14b and 14c show the binding of complexes of antibodies from the Fog-1 series to cells bearing FcγRIIIb of the allotypes NA1 and NA2 respectively. For both allotypes, binding is seen for the G1 antibody and, to a lesser extent, the G1Δa and G1Δc antibodies. No binding is observed for the other mutant antibodies since they show similar levels of fluorescence to the negative control samples of cross-linking F(ab')$_2$ alone or an aglycosyl IgG1 antibody complexed with the F(ab')$_2$.

EXAMPLE 7

Production of the Anti-HPA-1a Antibodies

The V$_H$ and V$_λ$ of the anti-HPA-1a scFv (Griffin, H. M. and Ouwehand, W. H. (1995) A human monoclonal antibody specific for the leucine-33 form of the platelet glycoprotein IIIa from a V gene phage display library. Blood 86, 4430-4436) were amplified and each attached to leader sequence from the vector M13VHPCR1 (Orlandi et al., 1989) by overlap extension PCR as described previously. DNA, 3' of the V$_H$ in M13VHPCR1 and representing the 5' end of the V$_H$-C$_H$ intron, was similarly joined to the leader/V$_H$DNA. The product was cloned as a HindIII-BamHI fragment into IgG1 and IgG2 expression vector to replace the existing variable region fragment and to give the vectors pSVgptB2VHHuIgG1 and pSVgptB2VHHuIgG2.

The leader Vλ DNA was joined in frame to the human λ chain constant region DNA of the Kern$^-$Oz$^-$ allotype (Rabbitts, T. H. Forster, H. and Matthews, J. G. 1983. *Mol. Biol. Med.* 1:11), taken from an existing expression vector (Routledge, E. G., Lloyd, I, Gorman, S. D., Clark, M. and Waldmann, H. 1991, *Eur. J. Immunol.* 21:2717). The whole λ gene was cloned into M13 as a HindIII-BamHI fragment and the murine heavy chain enhancer from pSVhyg-HuCK (Orlandi et al., 1989) added 5' of the gene using adapters so that the whole insert could be transferred to pSV2neo (Southern, P. J. and Berg. P. 1982. *J. Mol. Appl. Genet.* 1:327) as a BamHI fragment. The vector was designated pSVneoB2VλHuCλ.

The expression vectors were transfected into the rat myeloma cell line YB2/0, transfectants selected and antibody purified as described before. These B2IgG1 and B2IgG2 antibodies can be used as control antibodies.

Once the preferred null constant regions have been selected, the B2 VH HindIII-BamHI fragment can be introduced into expression vectors carrying the appropriate constant region genes, replacing the existing variable region fragment. The heavy chain expression vectors can then be co-transfected with pSVneoB2VλHuCλ into myeloma cells and the antibodies purified for use.

EXAMPLE 8

Therapeutic Use of Binding Molecule

A therapeutic molecule according to the present invention may be used to treat pregnancies complicated by HPA-1a alloimmunisation, for instance by intravenous administration to the mother, thereby relying on placental transfer (e.g. via the FcRn) to provide a therapeutic dose to the fetus.

An alternative is direct administration to the fetus by percutaneous umbilical vessel sampling. This procedure is currently performed in FAIT to deliver transfusions of compatible platelets. Because of the short survival of transfused platelets, the procedure may have to be repeated many times during the course of a pregnancy. It is however hazardous, with a risk of fetal loss of 0.5%/procedure.

However, fetal administration of a therapeutic antibody would have the advantage that a much lower dose is likely to be required, and therefore a combined approach using the molecules of the present invention in conjunction with platelet transfusion may be considered as a first step in therapy. This approach may reduce or eliminate the need for further platelet transfusions before delivery.

SUMMARY

The activities of the antibodies are summarised in Table 2 (FIG. 16). As can be seen, binding molecules have been produced which have reduced ability to bind to FcγRI, FcγRIIa 131H/H, FcγRIIa 131R/R, FcγRIIIb NA1 and FcγRIIIb NA2; are unable to trigger monocyte chemiluminescence; cannot mediate complement lysis and are not active in ADCC. However, the binding molecules retain binding to the inhibitory receptor, FcγRIIb. Other mutations previously used to knock out effector functions, such as removing the glycosylation site in the CH2 domain to make aglycosyl antibodies, may also eliminate binding to this receptor which may not be desirable.

Selected mutants have been shown to be able to inhibit completely the resetting of FcγRI-bearing cells by Fog-1 G1; the response of monocytes to Fog-1 G1-sensitised RBC; the response of monocytes to polyclonal anti-RhD-sensitised RBC; the killing of PBMC by complement lysis with CAMPATH-1 G1; the killing of RBC by ADCC with Fog-1 G1; the killing of RBC by ADCC with polyclonal anti-RhD serum.

The results herein demonstrate that altering even a single residue in an IgG CH2 domain to correspond to a different subclass can lead to different activities. Thus for the three pairs of Db and Dc mutants: G1Δb and G1Δc, G1Δab and G1Δac, G4Δb and G4Δc. Within each pair, the antibodies differ only by the absence (Δb) or presence (Δc) of G236. However, for most of the functions measured here, the Δb and Δc antibodies have different activities. The Db mutants are more active in binding to FcγRIIa 131H/H whereas the Dc mutants are more active in FcγRI binding, FcγRIIIb NA1 and NA2 binding, monocyte activation and ADCC. The region where the Δb and Δc mutations are made is known as the lower hinge or hinge link region and is likely to have an extended structure, connecting the hinge to the remainder of the CH2 domain. Addition or deletion of a residue from this region presumably alters the alignment of the lower hinge residues relative to receptor interaction sites in the remainder of the CH2 domain.

However it should be stressed that the effect of mutations cannot always be predicted from wildtype antibody activities, but will depend on the novel context (based on 'mixed' subclasses of IgG) in which the mutation is present. One example is in the assay of complement lysis where the activity of the IgG2 antibody is only about three-fold lower than that of IgG1 but introducing IgG2 residues into IgG1 (G1Δb and G1Δc) eliminates lysis. Similarly, IgG1 and IgG2 show equal binding to FcγRIIa 131H but G1Δb and G1Δc activities are 50- and 10-fold lower respectively. In the ADCC assays of FIGS. 9 and 10, IgG2 and IgG4 give similar, low but measurable levels of lysis. Substituting residues between IgG2 and IgG4, as well as into IgG1, reduces activity. These data suggest that the wildtype antibodies of the different human IgG subclasses and, presumably, the mutant antibodies may use different residues in binding to other molecules to trigger activities.

---

The invention claimed is:

1. A binding molecule which is a recombinant polypeptide comprising:
   (i) a binding domain capable of binding a target molecule, which binding domain is the binding site of an antibody, and
   (ii) an effector domain having an amino acid sequence homologous to a constant domain of a human immunoglobulin heavy chain;
   wherein the binding molecule is capable of binding the target molecule without triggering significant complement dependent lysis, or cell mediated destruction of the target, and the effector domain is capable of specifically binding FcγRIIb and optionally FcRn,
   and wherein the effector domain comprises a chimeric $C_H2$ domain which is derived from two or more human immunoglobulin heavy chain $C_H2$ domains, which human immunoglobulins are selected from IgG1, IgG2 and IgG4,
   and wherein the effector domain has a reduced affinity for FcγRI, FcγRIIa and FcγRIII and a reduced ability to mediate complement lysis by comparison with said constant domain of a human immunoglobulin heavy chain
   and wherein the chimeric $C_H2$ domain is a human immunoglobulin heavy chain $C_H2$ domain which has the following blocks of amino acids at the stated positions: 233P, 234V, 235A, 236G, 327G, 330S and 331S numbered with respect to the EU numbering system of Kabat, and is at least 98% identical to G1 Δac (SEQ ID NO:3) or G4 Δc (SEQ ID NO:12) as shown in FIG. 17.

2. The binding molecule as claimed in claim 1 wherein the chimeric $C_H2$ domain consists of G1Δac (SEQ ID NO:3) or G4Δc (SEQ ID NO:12) as shown in FIG. 17.

3. The binding molecule as claimed in claim 1 wherein the binding domain derives from a different source to the effector domain.

4. The binding molecule as claimed in claim 1 wherein the target molecule is selected from the group consisting of the RhD antigen of red blood cells; a human platelet antigen (HPA); a neutrophil antigen; a T-cell receptor; an integrin; a glomerular basement membrane (GBM) collagen type IV; a Der P1; VAP-1; laminin; lutheran; platelet glycoprotein VI; and platelet glyprotein Ia/IIa.

5. The binding molecule as claimed in claim 4 wherein the binding domain is the binding site of an antibody selected from the group consisting of anti-CD52; anti-RhD; anti-HPA-1a; anti-VAP-1; murine anti-α3 (IV) NC1; anti-CD3; anti-Der p I; anti-laminin; and anti-lutheran.

6. A preparation comprising the binding molecule as claimed in claim 1 plus a pharmaceutically acceptable carrier.

7. A binding molecule which is a recombinant polypeptide comprising:
   (i) a binding domain capable of binding a target molecule, which binding domain is the binding site of an antibody, and
   (ii) an effector domain having an amino acid sequence homologous to a constant domain of a human immunoglobulin heavy chain;
   wherein the binding molecule is capable of binding the target molecule without triggering significant complement dependent lysis, or cell mediated destruction of the target, and the effector domain is capable of specifically binding FcγRIIb and optionally FcRn,
   and wherein the effector domain comprises a chimeric $C_H2$ domain which is derived from two or more human immunoglobulin heavy chain $C_H2$ domains, which human immunoglobulins are selected from IgG1, IgG2 and IgG4,
   and wherein the effector domain has a reduced affinity for FcγRI, FcγRIIa and FcγRIII and a reduced ability to mediate complement lysis by comparison with said constant domain of a human immunoglobulin heavy chain
   and wherein the chimeric $C_H2$ domain is a human immunoglobulin heavy chain $C_H2$ domain which has the following blocks of amino acids at the stated positions: 233P, 234V, 235A and no residue at 236, 327G, 330S and 331S, numbered with respect to the EU system of Kabat, and is at least 98% identical to G1 Δab (SEQ ID NO:1) or G2 Δa (SEQ ID NO:2) as shown in FIG. 17.

8. A binding molecule which is a recombinant polypeptide comprising:
   (i) a binding domain capable of binding a target molecule, which binding domain is the binding site of an antibody, and
   (ii) an effector domain having an amino acid sequence homologous to a constant domain of a human immunoglobulin heavy chain;
   wherein the binding molecule is capable of binding the target molecule without triggering significant complement dependent lysis, or cell mediated destruction of the target, and the effector domain is capable of specifically binding FcγRIIb and optionally FcRn,
   and wherein the effector domain comprises a chimeric $C_H2$ domain which is derived from two or more human immunoglobulin heavy chain $C_H2$ domains, which human immunoglobulins are selected from IgG1, IgG2 and IgG4,
   and wherein the effector domain has a reduced affinity for FcγRI, FcγRIIa and FcγRIII and a reduced ability to mediate complement lysis by comparison with said constant domain of a human immunoglobulin heavy chain
   and wherein the chimeric $C_H2$ domain is a human immunoglobulin heavy chain $C_H2$ domain which has the following blocks of amino acids at the stated positions: 233P, 234V, 235A and no residue at 236, 327G, 330S and 331S, numbered with respect to the EU system of Kabat, and
   wherein the chimeric $C_H2$ domain consists of G1Δab (SEQ ID NO:1) or G2Δa (SEQ ID NO:2) as shown in FIG. 17.

9. The binding molecule as claimed in claim 7 wherein the binding domain derives from a different source to the effector domain.

10. The binding molecule as claimed in claim 7 wherein the target molecule is selected from the group consisting of the RhD antigen of red blood cells; a human platelet antigen (HPA); a neutrophil antigen; a T-cell receptor; an integrin; a glomerular basement membrane (GBM) collagen type IV; a Der P1; VAP-1; laminin; lutheran; platelet glycoprotein VI; and platelet glyprotein Ia/IIa.

11. The binding molecule as claimed in claim 10 wherein the binding domain is the binding site of an antibody selected from the group consisting of anti-CD52; anti-RhD; anti-HPA-1a; anti-VAP-1; murine anti-α3 (IV) NC1; anti-CD3; anti-Der p I; anti-laminin; and anti-lutheran.

12. A preparation comprising the binding molecule as claimed in claim 7 plus a pharmaceutically acceptable carrier.

13. The binding molecule as claimed in claim 5 wherein the anti-CD52 binding domain is CAMPATH-1; the anti-RhD is FOG1; the anti-Der p I is 2C7; the anti-CD3 is YTH12.5.

14. The binding molecule as claimed in claim 11 wherein the anti-CD52 binding domain is CAMPATH-1; the anti-RhD is FOG1; the anti-Der p I is 2C7; the anti-CD3 is YTH12.5.

15. The binding molecule as claimed in claim 4 wherein the HPA is HPA-1a.

16. The binding molecule as claimed in claim 10 wherein the HPA is HPA-1a.

17. A binding molecule which is a recombinant polypeptide comprising:
   (i) a binding domain capable of binding a target molecule, which binding domain is the binding site of an antibody, and
   (ii) an effector domain comprising chimeric $C_H2$ domain which consists of G1Δac (SEQ ID NO:3) as shown in FIG. 17.

18. A binding molecule which is a recombinant polypeptide comprising:
   (i) a binding domain capable of binding a target molecule, which binding domain is the binding site of an antibody, and
   (ii) an effector domain comprising chimeric $C_H2$ domain which consists of G4Δc (SEQ ID NO:12) as shown in FIG. 17.

19. A binding molecule which is a recombinant polypeptide comprising:
   (i) a binding domain capable of binding a target molecule, which binding domain is the binding site of an antibody, and
   (ii) an effector domain comprising chimeric $C_H2$ domain which consists of G1Δab (SEQ ID NO:1) as shown in FIG. 17.

20. A binding molecule which is a recombinant polypeptide comprising:
   (i) a binding domain capable of binding a target molecule, which binding domain is the binding site of an antibody, and
   (ii) an effector domain comprising chimeric $C_H2$ domain which consists of G2Δa (SEQ ID NO:2) as shown in FIG. 17.

21. An isolated nucleic acid comprising the nucleotide sequence encoding the effector domain of the binding molecule as claimed in claim 17, wherein said nucleic acid is DNA.

22. An isolated nucleic acid comprising the nucleotide sequence encoding the effector domain of the binding molecule as claimed in claim 18, wherein said nucleic acid is DNA.

23. An isolated nucleic acid comprising the nucleotide sequence encoding the effector domain of the binding molecule as claimed in claim 19, wherein said nucleic acid is DNA.

24. An isolated nucleic acid comprising the nucleotide sequence encoding the effector domain of the binding molecule as claimed in claim 20, wherein said nucleic acid is DNA.

25. An isolated nucleic acid comprising the nucleotide sequence encoding the effector domain of the binding molecule as claimed in claim 1, wherein said nucleic acid is DNA.

26. An isolated nucleic acid comprising the nucleotide sequence encoding the binding molecule as claimed in claim 1, wherein said nucleic acid is DNA.

27. The nucleic acid as claimed in claim 25 which is a replicable vector.

28. The nucleic acid as claimed in claim 27 wherein the nucleotide sequence is operably linked to a promoter.

29. An isolated host cell comprising or transformed with the vector of claim 28.

30. A process for producing a binding molecule which is a recombinant polypeptide comprising:
   (i) a binding domain capable of binding a target molecule, which binding domain is the binding site of an antibody, and
   (ii) an effector domain having an amino acid sequence homologous to a constant domain of a human immunoglobulin heavy chain;
   wherein the binding molecule is capable of binding the target molecule without triggering significant complement dependent lysis, or cell mediated destruction of the target, and the effector domain is capable of specifically binding FcγRIIb and optionally FcRn,
   and wherein the effector domain comprises a chimeric $C_H2$ domain which is derived from two or more human immunoglobulin heavy chain $C_H2$ domains, which human immunoglobulins are selected from IgG1, IgG2 and IgG4,
   and wherein the effector domain has a reduced affinity for FcγRI, FcγRIIa and FcγRIII and a reduced ability to mediate complement lysis by comparison with said constant domain of a human immunoglobulin heavy chain;
   the process comprising the steps of modifying a nucleotide sequence encoding a first human immunoglobulin heavy chain $C_H2$ domain such that 2 or 3 amino acids in at least 1 region of the $C_H2$ domain correspond to the amino acids from a second human immunoglobulin heavy chain $C_H2$ domain,
   wherein said modification introduces the following blocks of amino acids at the stated positions: 233P, 234V, 235A, 236G, 327G, 330S and 331S numbered with respect to the EU numbering system of Kabat
   and wherein said chimeric $C_H2$ domain is at least 98% identical to G1 Δac (SEQ ID NO:3) or G4 Δc (SEQ ID NO:12) as shown in FIG. 17,
   introducing into a host cell a vector comprising said modified nucleotide sequence,
   culturing said host cell under conditions such that said binding molecule is produced, and
   isolating said binding molecule from said cell culture.

31. A method of binding a target molecule, said method comprising contacting said target molecule with said binding molecule of claim 1 under conditions to allow binding.

32. The method of claim 31 wherein the effector domain specifically binds FcγRIIb, which binding causes inhibition of one or more of B cell activation; mast cell degranulation; and phagocytosis.

33. The method of claim 31 to inhibit the binding of a second binding molecule to the target molecule.

34. The method of claim 33 wherein the second binding molecule is an antibody.

35. The method of claim 31 wherein the target molecule is selected from the group consisting of the RhD antigen of red blood cells; a human platelet antigen (HPA); a neutrophil antigen; a T-cell receptor; an integrin; a glomerular basement membrane (GBM) collagen type IV; a Der P1; VAP-1; laminin; lutheran; platelet glycoprotein VI; and platelet glycoprotein Ia/IIa.

36. The method of claim 31 wherein said target molecule is in a patient suffering from a disorder selected from the group consisting of:
   i) Graft-vs-host disease, host-vs-graft disease, organ transplant rejection, bone-marrow transplant rejection, autoimmune vasculitis, arthritis or asthma, wherein the target molecule is a T-cell receptor;
   ii) autoimmune haemolytic anaemia or autoimmune thrombocytopenia, wherein the target molecule is selected from the group consisting of red blood cell Rhesus antigens D,C,c,E and e, the Kell (Kl) antigen and platelet glycoprotein GPIIb/IIIa and GPIb/IX/V;
iii) foetal/neonatal alloimmune thrombocytopenia, wherein the target molecule is human platelet antigen (HPA)-1a or platelet glycoprotein IIIa;
iv) dust mite allergy, wherein the target molecule is Der P1 protein of the house dust mite *Dermatophagoides pteronyssinus*;
v) Chrohn's, wherein the target molecule is VAP-1;
vi) haemolytic disease of the newborn (HDN), wherein the target molecule is selected from the group consisting of red blood cell Rhesus antigens D,C,c,E and e, and the Kell (Kl) antigen;
vii) Goodpastures, wherein the target molecule is non-collagenous (NC1) domain of α3(IV) collagen;
viii) sickle cell anaemia, wherein the target molecule is selected from the group consisting of: thrombospondin, laminin and lutheran; and
ix) coronary artery occlusion, wherein the target molecule is selected from the group consisting of integrin $\alpha_2\beta_1$ (platelet glycoprotein Ia/IIa) and non-integrin platelet glycoprotein VI.

37. The method of claim 31 wherein the contacting step is a step of administering the binding molecule to a patient, or optionally to the mother of the patient where the patient is an unborn infant.

38. An isolated nucleic acid comprising the nucleotide sequence encoding the effector domain of the binding molecule as claimed in claim 7, wherein said nucleic acid is DNA.

39. An isolated nucleic acid comprising the nucleotide sequence encoding the binding molecule as claimed in claim 7, wherein said nucleic acid is DNA.

40. The nucleic acid as claimed in claim 38 which is a replicable vector.

41. The nucleic acid as claimed in claim 40 wherein the nucleotide sequence is operably linked to a promoter.

42. An isolated host cell comprising or transformed with the vector of claim 41.

43. A process for producing a binding molecule which is a recombinant polypeptide comprising:
(i) a binding domain capable of binding a target molecule, which binding domain is the binding site of an antibody, and
(ii) an effector domain having an amino acid sequence homologous to a constant domain of a human immunoglobulin heavy chain;
wherein the binding molecule is capable of binding the target molecule without triggering significant complement dependent lysis, or cell mediated destruction of the target, and the effector domain is capable of specifically binding FcγRIIb and optionally FcRn,
and wherein the effector domain comprises a chimeric $C_H2$ domain which is derived from two or more human immunoglobulin heavy chain $C_H2$ domains, which human immunoglobulins are selected from IgG1, IgG2 and IgG4,
and wherein the effector domain has a reduced affinity for FcγRI, FcγRIIa and FcγRIII and a reduced ability to mediate complement lysis by comparison with said constant domain of a human immunoglobulin heavy chain;
the process comprising the steps of modifying a nucleotide sequence encoding a first human immunoglobulin heavy chain $C_H2$ domain such that 2, 3 or 4 amino acids in at least 1 region of the $C_H2$ domain correspond to the amino acids from a second human immunoglobulin heavy chain $C_H2$ domain, wherein said modification introduces the following blocks of amino acids at the stated positions: 233P, 234V, 235A and no residue at 236 and 327G, 330S and 331S numbered with respect to the ELU numbering system of Kabat
and wherein said chimeric $C_H2$ domain is at least 98% identical to G1 Δab (SEQ ID NO:1) or G2 Δa (SEQ ID NO:2) as shown in FIG. 17,
introducing into a host cell a vector comprising said modified nucleotide sequence,
culturing said host cell under conditions such that said binding molecule is produced, and
isolating said binding molecule from said cell culture.

44. The process as claimed in claim 43 wherein 2 amino acids in 1 region of the $C_H2$ domain are modified to the corresponding amino acids from the second human immunoglobulin heavy chain $C_H2$ domain.

45. A method of binding the target molecule, said method comprising contacting said target molecule with said binding molecule of claim 7 under conditions to allow binding.

46. The method of claim 45 wherein the effector domain specifically binds FcγRIIb, which binding causes inhibition of one or more of B cell activation; mast cell degranulation; and phagocytosis.

47. The method of claim 45 wherein the binding molecule inhibits the binding of a second binding molecule to the target molecule.

48. The method of claim 47 wherein the second binding molecule is an antibody.

49. The method of claim 45 wherein the target molecule is selected from the group consisting of the RhD antigen of red blood cells; an HPA alloantigen of platelets; a neutrophil antigen; a T-cell receptor; integrin; GBM collagen; Der P1; HPA-1a; VAP-1; laminin, lutheran; platelet glycoprotein VI; and platelet glycoprotein Ia/IIa.

50. The method of claim 45 wherein said target molecule is in a patient suffering from a disorder selected from the group consisting of:
i) Graft-vs-host disease, host-vs-graft disease, organ transplant rejection, bone-marrow transplant rejection, autoimmune vasculitis, arthritis or asthma, wherein the target molecule is a T-cell receptor;
ii) autoimmune haemolytic anaemia or autoimmune thrombocytopenia, wherein the target molecule is selected from the group consisting of red blood cell Rhesus antigens D,C,c,E and e, the Kell (Kl) antigen and platelet glycoprotein GPIIb/IIIa and GPIb/IX/V;
iii) foetal/neonatal alloimmune thrombocytopenia, wherein the target molecule is human platelet antigen (HPA)-1a or platelet glycoprotein IIIa;
iv) dust mite allergy, wherein the target molecule is Der P1 protein of the house dust mite *Dermatophagoides pteronyssinus*;
v) Chrohn's, wherein the target molecule is VAP-1;
vi) haemolytic disease of the newborn (HDN), wherein the target molecule is selected from the group consisting of red blood cell Rhesus antigens D,C,c,E and e, and the Kell (Kl) antigen;
vii) Goodpastures, wherein the target molecule is non-collagenous (NC1) domain of α3(IV) collagen;
viii) sickle cell anaemia, wherein the target molecule is selected from the group consisting of: thrombospondin, laminin and lutheran; and
ix) coronary artery occlusion, wherein the target molecule is selected from the group consisting of integrin $\alpha_2\beta_1$ (platelet glycoprotein Ia/IIa) and non-integrin platelet glycoprotein VI.

51. The method of claim 45 wherein the contacting step is a step of administering the binding molecule to a patient, or optionally to the mother of the patient where the patient is an unborn infant.

52. The method as claimed in claim 35 wherein the HPA is HPA-1a.

* * * * *

SEQUENCE LISTING

```
<160> NUMBER OF SEQ ID NOS: 27

<210> SEQ ID NO 1
<211> LENGTH: 109
<212> TYPE: PRT
<213> ORGANISM: Artificial Sequence
<220> FEATURE:
<223> OTHER INFORMATION: Description of Artificial Sequence: Mutated
      antibody

<400> SEQUENCE: 1

Ala Pro Pro Val Ala Gly Pro Ser Val Phe Leu Phe Pro Pro Lys Pro
  1               5                  10                  15

Lys Asp Thr Leu Met Ile Ser Arg Thr Pro Glu Val Thr Cys Val Val
             20                  25                  30

Val Asp Val Ser His Glu Asp Pro Glu Val Lys Phe Asn Trp Tyr Val
         35                  40                  45

Asp Gly Val Glu Val His Asn Ala Lys Thr Lys Pro Arg Glu Glu Gln
```

```
                50                  55                  60
Tyr Asn Ser Thr Tyr Arg Val Val Ser Val Leu Thr Val Leu His Gln
 65                  70                  75                  80

Asp Trp Leu Asn Gly Lys Glu Tyr Lys Cys Lys Val Ser Asn Lys Gly
                 85                  90                  95

Leu Pro Ser Ser Ile Glu Lys Thr Ile Ser Lys Ala Lys
                100                 105
```

<210> SEQ ID NO 2
<211> LENGTH: 109
<212> TYPE: PRT
<213> ORGANISM: Artificial Sequence
<220> FEATURE:
<223> OTHER INFORMATION: Description of Artificial Sequence: Mutated antibody

<400> SEQUENCE: 2

```
Ala Pro Pro Val Ala Gly Pro Ser Val Phe Leu Phe Pro Pro Lys Pro
 1               5                  10                  15

Lys Asp Thr Leu Met Ile Ser Arg Thr Pro Glu Val Thr Cys Val Val
                20                  25                  30

Val Asp Val Ser His Glu Asp Pro Glu Val Gln Phe Asn Trp Tyr Val
             35                  40                  45

Asp Gly Val Glu Val His Asn Ala Lys Thr Lys Pro Arg Glu Glu Gln
     50                  55                  60

Phe Asn Ser Thr Phe Arg Val Val Ser Val Leu Thr Val Val His Gln
 65                  70                  75                  80

Asp Trp Leu Asn Gly Lys Glu Tyr Lys Cys Lys Val Ser Asn Lys Gly
                 85                  90                  95

Leu Pro Ser Ser Ile Glu Lys Thr Ile Ser Lys Thr Lys
                100                 105
```

<210> SEQ ID NO 3
<211> LENGTH: 110
<212> TYPE: PRT
<213> ORGANISM: Artificial Sequence
<220> FEATURE:
<223> OTHER INFORMATION: Description of Artificial Sequence: Mutated antibody

<400> SEQUENCE: 3

```
Ala Pro Pro Val Ala Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
             35                  40                  45

Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys
                100                 105                 110
```

<210> SEQ ID NO 4
<211> LENGTH: 110
<212> TYPE: PRT

<213> ORGANISM: Homo sapiens

<400> SEQUENCE: 4

```
Ala Pro Glu Leu Leu Gly Gly Pro Ser Val Phe Leu Phe Pro Pro Lys
  1               5                  10                  15
Pro Lys Asp Thr Leu Met Ile Ser Arg Thr Pro Glu Val Thr Cys Val
             20                  25                  30
Val Val Asp Val Ser His Glu Asp Pro Glu Val Lys Phe Asn Trp Tyr
         35                  40                  45
Val Asp Gly Val Glu Val His Asn Ala Lys Thr Lys Pro Arg Glu Glu
     50                  55                  60
Gln Tyr Asn Ser Thr Tyr Arg Val Val Ser Val Leu Thr Val Leu His
 65                  70                  75                  80
Gln Asp Trp Leu Asn Gly Lys Glu Tyr Lys Cys Lys Val Ser Asn Lys
                 85                  90                  95
Ala Leu Pro Ala Pro Ile Glu Lys Thr Ile Ser Lys Ala Lys
            100                 105                 110
```

<210> SEQ ID NO 5
<211> LENGTH: 109
<212> TYPE: PRT
<213> ORGANISM: Homo sapiens

<400> SEQUENCE: 5

```
Ala Pro Pro Val Ala Gly Pro Ser Val Phe Leu Phe Pro Pro Lys Pro
  1               5                  10                  15
Lys Asp Thr Leu Met Ile Ser Arg Thr Pro Glu Val Thr Cys Val Val
             20                  25                  30
Val Asp Val Ser His Glu Asp Pro Glu Val Gln Phe Asn Trp Tyr Val
         35                  40                  45
Asp Gly Val Glu Val His Asn Ala Lys Thr Lys Pro Arg Glu Glu Gln
     50                  55                  60
Phe Asn Ser Thr Phe Arg Val Val Ser Val Leu Thr Val Val His Gln
 65                  70                  75                  80
Asp Trp Leu Asn Gly Lys Glu Tyr Lys Cys Lys Val Ser Asn Lys Gly
                 85                  90                  95
Leu Pro Ala Pro Ile Glu Lys Thr Ile Ser Lys Thr Lys
            100                 105
```

<210> SEQ ID NO 6
<211> LENGTH: 110
<212> TYPE: PRT
<213> ORGANISM: Homo sapiens

<400> SEQUENCE: 6

```
Ala Pro Glu Leu Leu Gly Gly Pro Ser Val Phe Leu Phe Pro Pro Lys
  1               5                  10                  15
Pro Lys Asp Thr Leu Met Ile Ser Arg Thr Pro Glu Val Thr Cys Val
             20                  25                  30
Val Val Asp Val Ser His Glu Asp Pro Glu Val Gln Phe Lys Trp Tyr
         35                  40                  45
Val Asp Gly Val Glu Val His Asn Ala Lys Thr Lys Pro Arg Glu Glu
     50                  55                  60
Gln Tyr Asn Ser Thr Phe Arg Val Val Ser Val Leu Thr Val Leu His
 65                  70                  75                  80
Gln Asp Trp Leu Asn Gly Lys Glu Tyr Lys Cys Lys Val Ser Asn Lys
                 85                  90                  95
```

Ala Leu Pro Ala Pro Ile Glu Lys Thr Ile Ser Lys Thr Lys
                100                 105                 110

<210> SEQ ID NO 7
<211> LENGTH: 110
<212> TYPE: PRT
<213> ORGANISM: Homo sapiens

<400> SEQUENCE: 7

Ala Pro Glu Phe Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
        50                  55                  60

Gln Phe Asn Ser Thr Tyr Arg Val Val Ser Val Leu Thr Val Leu His
 65                 70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
                100                 105                 110

<210> SEQ ID NO 8
<211> LENGTH: 110
<212> TYPE: PRT
<213> ORGANISM: Artificial Sequence
<220> FEATURE:
<223> OTHER INFORMATION: Description of Artificial Sequence: Mutated
      antibody

<400> SEQUENCE: 8

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
 65                 70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
                100                 105                 110

<210> SEQ ID NO 9
<211> LENGTH: 109
<212> TYPE: PRT
<213> ORGANISM: Artificial Sequence
<220> FEATURE:
<223> OTHER INFORMATION: Description of Artificial Sequence: Mutated
      antibody

<400> SEQUENCE: 9

Ala Pro Pro Val Ala Gly Pro Ser Val Phe Leu Phe Pro Pro Lys Pro
 1               5                  10                  15

```
Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys
            100                 105
```

<210> SEQ ID NO 10
<211> LENGTH: 110
<212> TYPE: PRT
<213> ORGANISM: Artificial Sequence
<220> FEATURE:
<223> OTHER INFORMATION: Description of Artificial Sequence: Mutated antibody

<400> SEQUENCE: 10

```
Ala Pro Pro Val Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 11
<211> LENGTH: 109
<212> TYPE: PRT
<213> ORGANISM: Artificial Sequence
<220> FEATURE:
<223> OTHER INFORMATION: Description of Artificial Sequence: Mutated antibody

<400> SEQUENCE: 11

```
Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser Gln Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Gly
                85                  90                  95
```

```
Leu Pro Ser Ser Ile Glu Lys Thr Ile Ser Lys Ala Lys
            100                 105
```

```
<210> SEQ ID NO 12
<211> LENGTH: 110
<212> TYPE: PRT
<213> ORGANISM: Artificial Sequence
<220> FEATURE:
<223> OTHER INFORMATION: Description of Artificial Sequence: Mutated
      antibody

<400> SEQUENCE: 12
```

```
Ala Pro Pro Val Ala Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110
```

```
<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13
ggatgcaggc tactcgaggg cacctg                                          26

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14
tgtccatgtg gccctggtac cccacgggt                                       29

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15
gagcctgctt cctctagaca ccctccct                                        28

<210> SEQ ID NO 16
<211> LENGTH: 36
<212> TYPE: DNA
<213> ORGANISM: Artificial Sequence
```

```
<220> FEATURE:
<223> OTHER INFORMATION: Description of Artificial Sequence:
      Oligonucleotide

<400> SEQUENCE: 16
tctccaacaa aggcctcccg tcctccatcg agaaaa                                36

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 17
ttttctcgat ggaggacggg aggcctttgt tggaga                                36

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 18
tcctcagcac ctccagtcgc gggggggaccg tcagtc                               36

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 19
gactgacggt cccgcgactg gaggtgctga gga                                   33

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 20
caggtgccct cgagtagcct gcatcc                                           26

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 21
tccacaggtg tccactccca ggtgcatcta cagcag                                36

<210> SEQ ID NO 22
<211> LENGTH: 37
<212> TYPE: DNA
<213> ORGANISM: Artificial Sequence
<220> FEATURE:
```

<223> OTHER INFORMATION: Description of Artificial Sequence:
      Oligonucleotide

<400> SEQUENCE: 22
gaggttgtaa ggactcacct gaggagacgg tgaccgt                                37

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 23
tccacaggtg tccactccga catccagatg acccag                                 36

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 24
gaggttgtaa ggactcacgt ttgatctcca gcttggt                                37

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 25
ggagtggaca cctgtggaga                                                   20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 26
gtgagtcctt acaacctctc                                                   20

<210> SEQ ID NO 27
<211> LENGTH: 6
<212> TYPE: PRT
<213> ORGANISM: Homo sapiens

<400> SEQUENCE: 27

Glu Leu Leu Gly Gly Pro
 1               5